US006410732B2

(12) United States Patent
Akhavan-Tafti et al.

(10) Patent No.: US 6,410,732 B2
(45) Date of Patent: Jun. 25, 2002

(54) PROCESSING AND SYNTHETIC INTERMEDIATES FOR PREPARING N-ARYLACRIDANCARBOXYLIC ACID DERIVATIVES

(75) Inventors: Hashem Akhavan-Tafti, Howell; Robert A. Eickholt, Troy; Richard S. Handley, Canton, all of MI (US)

(73) Assignee: Lumigen, Inc., Southfield, MI (US)

( * ) Notice: Subject to any disclaimer, the term of this patent is extended or adjusted under 35 U.S.C. 154(b) by 0 days.

(21) Appl. No.: 09/770,015

(22) Filed: Jan. 25, 2001

Related U.S. Application Data

(63) Continuation-in-part of application No. 09/557,726, filed on Apr. 26, 2000, now Pat. No. 6,296,787, which is a continuation of application No. 09/358,002, filed on Jul. 21, 1999, now Pat. No. 6,090,571, which is a division of application No. 08/894,143, filed on Aug. 13, 1997, now Pat. No. 6,045,727, which is a continuation-in-part of application No. 08/585,090, filed on Jan. 16, 1996, now abandoned, and a continuation-in-part of application No. 08/683,927, filed on Jul. 19, 1996, now abandoned.

(51) Int. Cl.[7] .................. C07D 219/02; C07D 401/04
(52) U.S. Cl. ................. 546/102; 546/23; 546/103; 546/104
(58) Field of Search .................. 546/102, 103, 546/104, 23

(56) References Cited

U.S. PATENT DOCUMENTS

| | | | |
|---|---|---|---|
| 5,523,212 A | | 6/1996 | Akhavan-Tafti |
| 5,593,845 A | | 1/1997 | Akhavan-Tafti |
| 5,686,258 A | * | 11/1997 | Akhavan-Tafti et al. ... 435/7.91 |
| 5,929,281 A | | 7/1999 | Nishiyama |
| 6,030,803 A | | 2/2000 | Jacquemijns |
| 6,162,610 A | | 12/2000 | Bronstein |

OTHER PUBLICATIONS

Wolfe, J. Org. Chem. 65, 1158–1174 (2000).
Huang, Organic Lett. 1(8), 1307–1309 (1989).
Guram, Angew. Chem. Int. Ed. Engl. 34(12), 1348–1350 (1995).
Hartwig, J. Org. Chem. 64, 5575–5580 (1999).
Wolfe, J. Org. Chem. 65, 1144–1157 (2000).
Gagan, Acridines, R.M. Acheson, Ed., Wiley (1973) Chapt. III, "9–Acridones", pp. 141–197.

* cited by examiner

Primary Examiner—Charanjit S. Aulakh
(74) Attorney, Agent, or Firm—Richard S. Handley

(57) ABSTRACT

Synthetic processes and intermediates are disclosed for the preparation of N-arylacridancarboxylic acid derivatives. The derivatives are esters, thioesters, amides and sulfonimides. A key feature of the processes is the preparation of N-aryl substituted intermediates by formation of a bond between the nitrogen atom of the acridan ring and a carbon atom of another aromatic or heteroaromatic ring compound. The arylation reaction is catalyzed by a palladium catalyst. The N-arylacridancarboxylic acid derivatives are useful in methods for producing light and in assays for peroxidase enzymes and enzyme inhibitors and in assays employing enzyme-labeled specific binding pairs.

50 Claims, No Drawings

PROCESSING AND SYNTHETIC INTERMEDIATES FOR PREPARING N-ARYLACRIDANCARBOXYLIC ACID DERIVATIVES

CROSS REFERENCE TO RELATED APPLICATION

This application is a continuation-in-part of applicant's application Ser. No. 09/557,726 filed on Apr. 26, 2000 now U.S. Pat. No. 6,296,787 which is a continuation of allowed U.S. application Ser. No. 09/358,002 filed on Jul. 21, 1999, now U.S. Pat. No. 6,090,571 which is a division of U.S. appication Ser. No. 08/894,143 filed on Aug. 13, 1997 as a result of National Stage entry from PCT application US 97/00015, now U.S. Pat. No. 6,045,727 which is a continuation-in-part of U.S. application Ser. No. 08/585,090, filed Jan. 16, 1993 abandoned and 08/683,927 filed Jul. 19, 1996, abandoned.

FIELD OF THE INVENTION

This invention relates to synthetic processes and intermediates useful for preparing N-arylacridancarboxylic acid derivatives. The N-arylacridancarboxylic acid derivatives are useful in methods to produce chemiluminescence, for example by reaction with a peroxide and a peroxidase. The chemiluminescent reaction is useful in methods of analysis for detecting peroxidase enzymes or hydrogen peroxide. It is also useful in methods to detect and quantify various biological molecules wherein a peroxidase is used as a label and in methods to detect oxidase enzymes which generate hydrogen peroxide.

BACKGROUND OF THE INVENTION

The detection and quantitation of biological molecules has been accomplished historically with excellent sensitivity by the use of radiolabeled reporter molecules. Recently numerous non-radioactive methods have been developed to avoid the hazards and inconvenience posed by these materials. Methods based on enzyme-linked analytes offer the best sensitivity since the ability to catalytically turn over substrate to produce a detectable change achieves an amplification. Substrates which generate color, fluorescence or chemiluminescence have been developed, the latter achieving the best sensitivity.

Further increases in assay sensitivity will expand the range of utility of chemiluminescence-based methods by permitting the detection of analytes present in smaller quantities or reducing the amount of time and/or reagents required to perform the assay. A way to increase the speed and sensitivity of detection in an enzymatic chemiluminescent assay is through the use of substrates which generate light with a higher efficiency or for a greater length of time.

Among the enzymes used in enzyme-linked detection methods such as immunoassays, detection of oligonucleotides and nucleic acid hybridization techniques, the most extensively used to date has been horseradish peroxidase. Chemiluminescent reagents known in the art do not permit full advantage to be taken of the beneficial properties of this enzyme in analysis mainly due to sensitivity limitations. A reagent which permits the detection of lower amounts of enzyme is needed to enable the use of peroxidase conjugates in applications requiring ultrasensitive detection. Specifically, reagents are required which generate higher levels of chemiluminescence without an accompanying increase in the background or non-specific chemiluminescence. The increased chemiluminescence can be accomplished via either a higher maximum intensity or a longer duration than compounds known in the art.

a. Enzymatic oxidation of N-alkylacridancarboxylic acid derivatives. Applicants' U.S. Pat. Nos. 5,491,072, 5,523,212, 5,593,845, 5,670,644, 5,723,295 and 5,750,698 disclose the use of a peroxidase enzyme to oxidize substituted and unsubstituted N-alkylacridancarboxylic acid derivatives to generate chemiluminescence. In the presence of a peroxidase enzyme and a peroxide, N-alkylacridancarboxylic acid derivatives are efficiently oxidized to produce the N-alkylacridone and blue chemiluminescence. N-aryl-substituted acridan-carboxylic acid derivatives are not disclosed.

U.S. Pat. No. 6,030,803 discloses a group of acridancarboxylic acid derivatives having a substituted alkoxy or alkylthio leaving group but not aryloxy or arylthio leaving groups as chemiluminescent substrate for peroxidase enzymes. N-aryl acridan compounds are claimed but no examples of N-aryl compounds are provided. All exemplary compounds contain a methyl group as the substituent on the acridan ring nitrogen atom. U.S. Pat. No. 6,162,610 discloses a group of acridancarboxylic acid derivatives having a substituted alkoxy, alkylthio or amide leaving group as chemiluminescent substrate for peroxidase enzymes. The claimed compounds bear a group designated —OX alleged to be a triggering group. No examples of N-aryl compounds are provided nor is a basis for the alleged triggering effect.

N-arylacridancarboxylic acid derivatives having a heteroaromatic group bound to the nitrogen atom are not taught or suggested in this or any of the cited publications nor in any other publication prior to the present invention.

OBJECTS

It is therefore an object of the present invention to provide processes for the synthesis of N-arylacridancarboxylic acid derivatives for use in generating chemiluminescence. It is another object of the present invention to provide synthetic intermediates useful in methods for preparing N-arylacridancarboxylic acid derivatives. It is still another object of the present invention to provide N-arylacridancarboxylic acid derivatives for use in generating chemiluminescence. It is also an object of the present invention to provide N-arylacridancarboxylic acid derivatives for use in methods of analysis and detection. It is a further object to provide chemiluminescent methods for the detection of biological materials and compounds. It is also an object of the present invention to provide a chemiluminescent method for detecting peroxidase enzymes and enzyme-conjugates. Additionally, it is an object of the present invention to provide improved methods for use in solution or on surfaces in nucleic acid assays, protein-binding assays, Western blots, Southern blots and other DNA and RNA hybridization assays and for detection of haptens, proteins and antibodies in enzyme immunoassays.

DESCRIPTION OF THE PREFERRED EMBODIMENTS

Definitions

The term "substituted" when used to describe an organic moiety such as a chain or ring group refers to the replacement of one or more hydrogen atoms on the chain or ring with another atom or group. Exemplary groups include halogen, trihalomethyl, nitro, nitroso, cyano, ammonium, hydrazinyl, carboxyl, carboxamide, carboalkoxy, formyl (—CHO), keto, amino, substituted amino, imino, amido, aryl, alkyl, perfluoroalkyl, alkenyl, alkynyl, alkoxy, hydroxy, sulfhydryl, alkylthio, sulfate, sulfonate, phosphonium, phosphate and phosphonate groups.

The term "leaving group ability" as used herein refers to the propensity for a group when attached to the carbonyl group of the acridancarboxylic acid derivative to be displaced in the nucleophilic reaction of the invention involving a peroxide or hydroperoxide or its anion.

The present invention relates to N-arylacridancarboxylic acid derivatives of the formula:

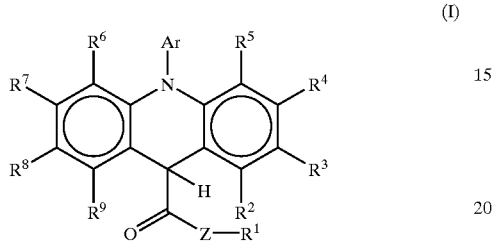

wherein $R^1$ is selected from alkyl, substituted alkyl, heteroalkyl, aralkyl, substituted aralkyl, aryl, substituted aryl and heteroaryl groups, $R^2$ to $R^9$ are independently selected from substituents which contain from 1 to 50 atoms selected from C, H, N, O, S, P and halogen atoms, wherein Ar is an aryl, substituted aryl or heteroaryl group and Z is selected from O and S atoms or the group $ZR^1$ is an —$NR^{10}R^{11}$ group wherein $R^{10}$ and $R^{11}$ are independently selected from alkyl, substituted alkyl, aryl, substituted aryl, aralkyl, alkylsulfonyl and arylsulfonyl groups, and wherein $R^{10}$ and $R^{11}$ can be combined with N into a heterocycle with leaving group ability including pyrazole, imidazole, benzimidazole, triazole, benzotriazole, tetrazole, oxazole, benzoxazole, thiazole and benzothiazole.

When $R^{10}$ or $R^{11}$ is alkylsulfonyl or arylsulfonyl it is preferably selected from methanesulfonyl, trifluoromethanesulfonyl, benzenesulfonyl or substituted benzenesulfonyl and the other of $R^{10}$ or $R^{11}$ is preferably an alkyl, phenyl or substituted phenyl group. When $R^1$ is a substituted alkyl or substituted aryl group the group is preferably substituted with one or more electron withdrawing groups, preferably halogen atoms and most preferably with fluorine.

Compounds having Formula I which contain an N-aryl group are useful in methods for producing chemiluminescence. These compounds distinguish from known prior art compounds which all have an alkyl group substituted on the ring nitrogen atom, usually a methyl group. In contrast, the compounds of the present invention bear an aromatic or heteroaromatic ring group on the ring nitrogen. Representative aryl groups include phenyl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl and pyrrolyl groups. The aryl or heteroaryl group can be substituted with one or more substituents as defined above and which allows or does not interfere with or prevent the production of light from reaction of the N-arylacridan-carboxylic acid derivative with an oxidant. Representative substituents which can be present on the aryl group include without limitation, halogen, trihalomethyl, nitro, nitroso, cyano, ammonium, hydrazinyl, carboxyl, carboxamide, carboalkoxy, formyl (—CHO), keto, amino, substituted amino, imino, amido, aryl, alkyl, perfluoroalkyl, alkenyl, alkynyl, alkoxy, hydroxy, sulfhydryl, alkylthio, sulfate, sulfonate, phosphonium, phosphate and phosphonate.

Examples of some preferred compounds are:

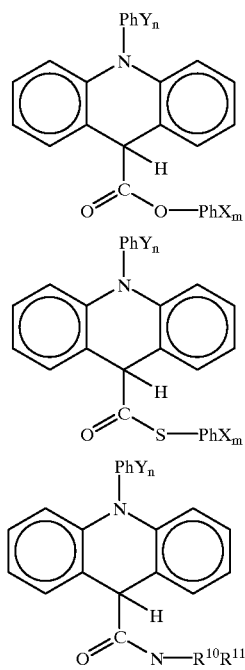

wherein X is an electron withdrawing group, Y is a non-hydrogen substituent and wherein m and n are each integers from 0 to 5 and $R^{10}$ and $R^{11}$ are as defined above. Preferably $R_{10}$ is alkylsulfonyl or arylsulfonyl and $R^{11}$ is alkyl or aryl. Preferred electron withdrawing groups are halogen atoms, more preferably chlorine or fluorine atoms. The number of such electron withdrawing groups m is preferably at least one and more desirably at least two.

Another class of preferred compounds is:

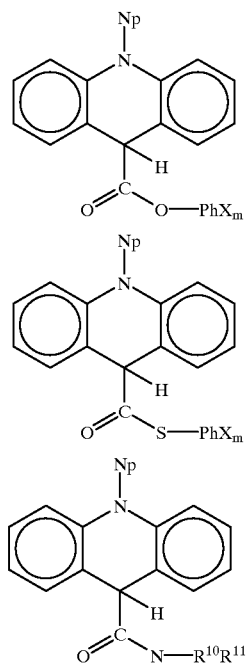

wherein X, m, $R^{10}$ and $R^{11}$ are as defined above and Np is a naphthyl group.

Yet other preferred compounds have the formula:

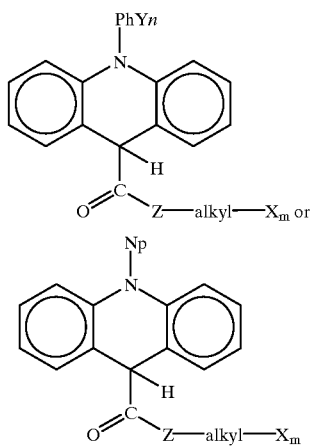

wherein alkyl-$X_m$ is a substituted alkyl and X, Y and m and n are as defined above and Z is O or S.

The present invention further relates to novel processes and synthetic intermediates which are used to prepare the N-arylacridancarboxylic acid derivatives. Applicants have discovered new processes for preparing N-arylacridancarboxylic acid derivatives (I)

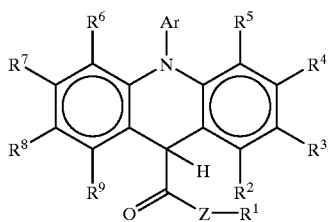

beginning from acridone or a ring-substituted acridone compound having the formula:

Where not commercially available, acridones can be prepared by art-known methods including 1) cyclization of 2-amino-2'-halobenzophenone derivatives, 2) cyclization of diphenylamine-2-carboxylic acids, 3) hydrolysis of 9-chloroacridines and 9-methoxyacridines and 4) rearrangement of 3-phenylanthranils as described in *Acridines*, R. M. Acheson, ed. Wiley, (1973) Chapter III, pp. 143–196. The acridone compound is reduced to the corresponding acridan by reduction of the ketone moiety. Reduction can be achieved with known reagents for ketone reductions as disclosed In the aforementioned *Acridines*, pp. 201–2, including Na/Hg amalgam, Al/Hg amalgam, copper chromite, $NH_2NH_2$, base and ethylene glycol. In another method the acridone is converted to the 9-chloroacridine compound and then reduced with Raney nickel. In addition, the ketone can be reduced with hydride reducing agents such as $LiAlH_4$.

The substituted or unsubstituted acridan compound thus formed is converted to the N-arylacridancarboxylic acid derivative by a process involving an N-arylation reaction and a reaction process for attaching the carboxylic acid derivative moiety —C(=O)$ZR^1$. The arylation and carboxylate attaching steps can be performed at different points in the synthetic scheme as described in more detail below.

In a first embodiment of the synthetic process, the acridan compound is reacted with an arylating compound selected from aryl halides and sulfonate esters in an inert solvent in the presence of a base and a palladium catalyst to form an N-arylacridan compound.

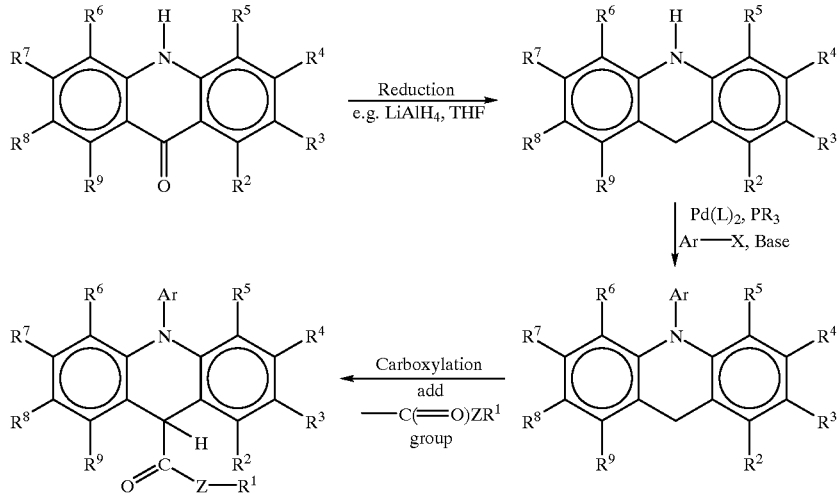

In this context aryl includes both aromatic and heteroaromatic ring compounds. Halides include iodide, bromide and chloride. Sulfonate esters include trifluoromethanesulfonates (triflates) and other esters active as leaving groups. Preferred palladium catalysts are prepared from a divalent palladium compound $PdL_2$ and a tertiary phosphine $PR_3$ wherein each R is independently selected from alkyl and aryl groups Suitable divalent compounds $PdL_2$ include any divalent palladium compound with labile ligands selected from carboxylate esters, halogens and ketones and include palladium acetate, palladium chloride, palladium bis(dibenzylideneacetone) $Pd(dba)_2$ and $Pd_2(dba)_3$. Suitable tertiary phosphines include trialkylphosphines such as $P(t-Bu)_3$, triaryl phosphines such as BINAP and mixed alkylarylphosphines such as DPPE, DPPF, DPPB and DPPP. Bases include $KHPO_4$, $CsCO_3$, and alkoxide salts such as sodium t-butoxide. Inert solvents useful in this step include toluene, benzene, THF, DME, diglyme and the like. The solvent preferably has a boiling point above about 50° C. to enable heating of the reaction. However the reaction can be performed at room temperature or elevated temperatures.

The N-arylacridan compound is then converted to an N-arylacridancarboxylic acid derivative by a carboxylation reaction in which a carbonyl-containing group is attached to the 9-position of the acridan ring. The carbonyl-containing group can be a carboxyl group (—COOH) or its salt, a carboxyl ester group (—$COOR^1$), a thioester group (—$COSR^1$) or an amide group (—$CONR^{10}R^{11}$). Conversion of the N-arylacridan to the carboxylic acid derivative involves formation of the acridan anion at the 9-position by treatment with a strong base and then reaction with a reagent to attach the carbonyl-containing group.

This conversion can be accomplished in two steps by reaction of the N-arylacridan with a base to generate the anion at the 9-position and capture of the anion with $CO_2$ to produce the N-arylacridancarboxylic acid or its salt. The N-arylacridancarboxylic acid is subsequently converted to any of the various acid derivatives (I) having the group $Z-R^1$ by reaction of the N-arylacridancarboxylic acid with a compound $HZ-R^1$ where Z and $R^1$ are as defined above. Preferably a coupling agent is used to promote the conversion of the acid to the acid derivative. In one embodiment the N-arylacridancarboxylic acid is first converted to the acid chloride by methods generally known in the art such as by use of thionyl chloride ($SOCl_2$) or $PCl_3$. The acid chloride is reacted with a compound of the formula $HZ-R^1$ in the presence of a base or with a salt of the compound $HZ-R^1$. In another embodiment the acid is coupled to the compound $HZ-R^1$ with the aid of a carbodiimide coupling agent such as dicyclohexylcarbodiimide or with carbonyl diimidazole, CDI. In other embodiments strong acids or bases are used as the coupling agent to catalyze the formation of the acid derivative.

Conversion of the N-arylacridan to the N-arylacridancarboxylic acid derivative can also be accomplished in one step by reaction of the 9-position anion described above with a reagent having the formula $X-CO-ZR^1$ which attaches one of the ester (—$COOR^1$), thioester (—$COSR^1$) or amide (—$CONR^{10}R^{11}$) groups directly. Suitable reagents have a leaving group X such as a halogen attached to the carbonyl group of the carboxylating agent. Suitable reagents would therefore include chloroformate esters (Cl—$COOR^1$), chlorothioformate esters (Cl—$COSR^1$) and carbamoyl chlorides (Cl—$CONR^{10}R^{11}$).

The present invention further relates, in a second embodiment, to a synthetic process for preparing an N-arylacridancarboxylic acid derivative (I) in which the N-arylation step is performed after formation of the acridancarboxylic acid or acid derivative. In an exemplary process (a) an acridan-9-carboxylic acid derivative or an acridan-9-carboxylic acid is reacted with an arylating agent and a palladium catalyst as described above to effect N-arylation. When the N-arylation reaction is performed on the carboxylic acid, the product N-arylacridancarboxylic acid is then converted to the acid derivative (I) by reaction with a compound $HZ-R^1$ where Z and $R^1$ are as defined above. Preferably a coupling agent as described above is used to promote the conversion of the acid to the acid derivative.

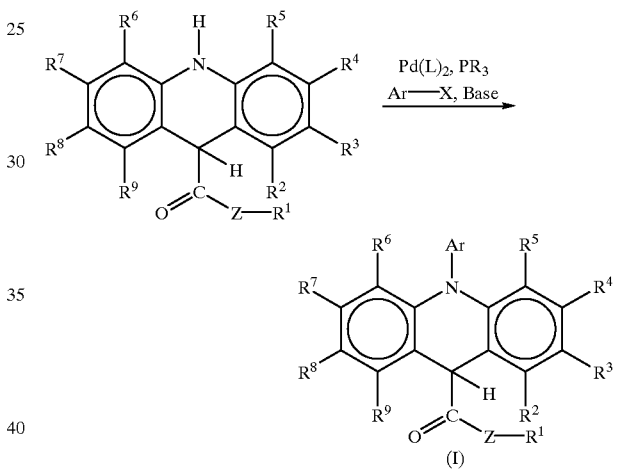

Acridine-9-carboxylic acid is available commercially and can be prepared using methods known to one of skill in the art of organic chemistry by consultation of the scientific literature. Ring substituted acridan-9-carboxylic acids can similarly be prepared by like methods.

The present invention further relates, in a third embodiment, to a synthetic process for preparing an N-arylacridancarboxylic acid derivative (I) in which the acridone or ring-substituted acridone undergoes the N-arylation step according to the above-described N-arylation reaction method. The N-arylacridone intermediate is then reduced to the corresponding N-arylacridan by reduction of the ketone moiety according to one of the methods described above. The N-arylacridan compound is then converted to an N-arylacridancarboxylic acid derivative by a carboxylation reaction in which a carbonyl-containing group is attached to the 9-position of the acridan ring via either the one step or two step processes as described above

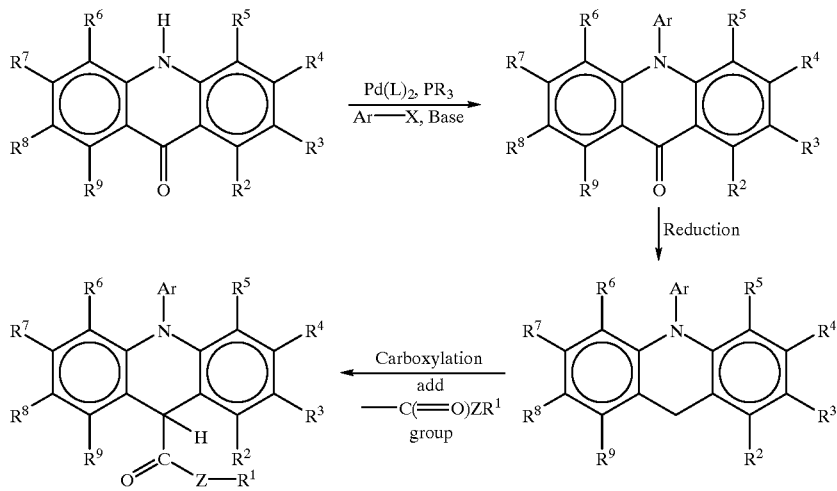

Another aspect of the present invention relates to synthetic intermediates used in preparing N-arylacridancarboxylic acid derivatives. In particular, N-arylacridancarboxylic acid compounds (II) and their carboxylate salts are claimed wherein $R^2$ to $R^9$ are independently selected from substituents which contain from 1 to 50 atoms selected from C, H, N, O, S, P and halogen atoms, wherein Ar is an aryl, substituted aryl or heteroaryl group.

(II)

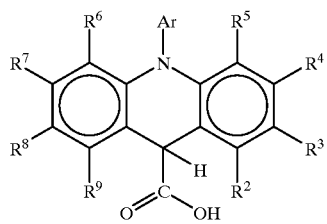

Representative aryl groups include phenyl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl and pyrrolyl groups. The aryl or heteroaryl group can be substituted with one or more substituents defined as defined above and which allows or does not interfere with or prevent the production of light from the N-arylacridancarboxylic acid derivative when it is reacted with a peroxide and a peroxidase. Preferably, Ar is selected from phenyl, substituted phenyl and naphthyl groups. Representative substituents which can be present on the aryl group include without limitation, halogen, trihalomethyl, nitro, nitroso, cyano, ammonium, hydrazinyl, carboxyl, carboxamide, carboalkoxy, formyl (—CHO), keto, amino, substituted amino, imino, amido, aryl, alkyl, perfluoroalkyl, alkenyl, alkynyl, alkoxy, hydroxy, sulfhydryl, alkylthio, sulfate, sulfonate, phosphonium, phosphate and phosphonate. In preferred compounds of formula (II) each of $R^2$ to $R^9$ are hydrogen or one of $R^2$ to $R^9$ is an alkoxy group and each of the others is hydrogen. When compound (II) is present in the form of a salt, the counter ion will be the same as the counter ion of the strong base used in the carboxylation reaction. Preferred counter ions include alkali metal ions.

Another aspect of the present invention relates to reaction of N-arylacridancarboxylic acid derivatives (I) of the present invention with an oxidant to generate visible chemiluminescence. In one embodiment, reaction of an N-arylacridancarboxylic acid derivative with a base which can remove the proton at the 9-position of the acridan ring, i.e. the proton α to the carbonyl, in the presence of molecular oxygen in an aprotic solvent produces chemiluminescence. Suitable bases include, hydroxide salts, alkoxide salts such as sodium methoxide and potassium t-butoxide, and tetraalkylammonium fluoride. Aprotic solvents useful include dimethyl sulfoxide, dimethylformamide, dimethylacetamide and tetrahydrofuran.

In another method, reaction of an N-arylacridancarboxylic acid derivative with an oxidant system comprising a peroxide and a peroxidase enzyme produces chemiluminescence. This reaction system is highly useful for assay applications. The chemiluminescence is believed to arise from the excited state of N-arylacridone or the substituted N-arylacridone product as shown in the generalized reaction below.

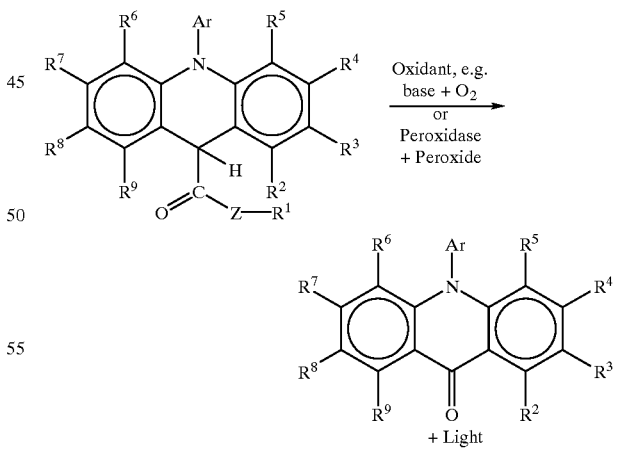

Compounds of the present invention typically produce light over a 100–200 nm wide band of emission, which exhibits a maximum intensity at wavelengths in the near ultraviolet to the visible region of the electromagnetic spectrum. Typical wavelengths of maximum intensity $\lambda_{max}$ are in the range of 350–500 nm. It is contemplated that compounds of formula I bearing a covalently linked fluorophore could undergo intramolecular energy transfer resulting in emission at longer wavelengths from the excited state of the fluorophore.

The peroxidase which can undergo the chemiluminescent reaction include lactoperoxidase, microperoxidase, myeloperoxidase, haloperoxidase, e.g. vanadium bromoperoxidase, horseradish peroxidase, fungal peroxidases such as lignin peroxidase and peroxidase from Arthromyces ramosus and Mn-dependent peroxidase produced in white rot fungi, and soybean peroxidase. Other peroxidase mimetic compounds which are not enzymes but possess peroxidase-like activity including iron complexes and Mn-TPPS$_4$ (Y.-X. Ci, et al., Mikrochem. J., 52, 257–62 (1995)) are explicitly considered to be within the scope of the meaning of peroxidase as used herein. Conjugates or complexes of a peroxidase and a biological molecule can also be used in the method for producing chemiluminescence, the only proviso being that the conjugate display peroxidase activity. Biological molecules which can be conjugated to one or more molecules of a peroxidase include DNA, RNA, oligonucleotides, antibodies, antibody fragments, antibody-DNA chimeras, antigens, haptens, proteins, lectins, avidin, streptavidin and biotin. Complexes including or incorporating a peroxidase such as liposomes, micelles, vesicles and polymers which are functionalized for attachment to biological molecules can also be used in the methods of the present invention.

Compounds of the present invention are useful in a reagent composition which generates light in the presence of a peroxidase. Compositions comprise the acridan and a peroxide compound in aqueous solution, preferably a buffer solution, wherein the peroxide participates in the reaction of the acridan with the peroxidase. Optionally the composition can comprise any or all of the following additional components:

a compound which enhances light production from the chemiluminescent reaction;

a chelating agent which prevents the peroxide compound from reacting prior to addition of the peroxidase to the composition; and/or a surfactant including nonionic, anionic and cationic compounds including monomeric or polymeric compounds.

The peroxide component is any peroxide or alkyl hydroperoxide capable of reacting with the peroxidase. Preferred peroxides include hydrogen peroxide, urea peroxide, and perborate salts.

Suitable buffers include any of the commonly used buffers capable of maintaining a pH in the range of about 6 to about 10 for example, phosphate, borate, carbonate, tris (hydroxymethylamino)methane, glycine, tricine, 2-amino-2-methyl-1-propanol, diethanolamine and the like.

Chemiluminescence enhancing compounds usable include art-known compounds which promote the reactivity of the enzyme. Included among these enhancers are phenolic compounds and aromatic amines known to enhance other peroxidase reactions as described in G. Thorpe, L. Kricka, in *Bioluminescence and Chemiluminescence, New Perspectives*, J. Scholmerich, et al, Eds., pp. 199–208 (1987), M. Ii, H. Yoshida, Y. Aramaki, H. Masuya, T. Hada, M. Terada, M. Hatanaka, Y. Ichimori, *Biochem. Biophys. Res. Comm.*, 193(2), 540–5 (1993), and in U.S. Pat. Nos. 5,171,668 and 5,206,149 which are incorporated herein by reference. Substituted and unsubstituted arylboronic acid compounds and their ester and anhydride derivatives as disclosed in U.S. Pat. Nos. 5,512,451 and 5,629,168, incorporated herein by reference, are also considered to be within the scope of enhancers useful in the present invention. Yet other enhancer compounds are taught in U.S. Pat. Nos. 5,171,668 and 5,206,149. Also included are phenothiazine and phenoxazine compounds as taught in PCT Publication WO97/39142. Preferred enhancers include but are not limited to: p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol. Mixtures of more than one enhancer from those classes mentioned above can also be employed. These enhancer compounds are thought to act as co-substrates for the peroxidase and undergo a reversible oxidation.

Chelating agents include cation complexing agents wherein the agent can be selected from the group consisting of chelating agents such as ethylenediaminetetraacetic acid (EDTA), diethylenetriaminepentaacetic acid (DTPA), or ethylenebis(oxyethylenenitrilo)tetraacetic acid (EGTA) and their salts.

Additives which suppress the generation of chemiluminescence from the reaction of hydrogen peroxide and N-arylacridancarboxylic acid derivatives in the absence of peroxidase enzymes are employed to further improve the utility of the invention. It has also been found that certain surfactants including anionic surfactants such as sodium dodecyl sulfate (SDS), cationic surfactants and nonionic surfactants such as polyoxyethylenated alkylphenols, polyoxyethylenated alcohols, polyoxyethylenated ethers, polyoxyethylenated sorbitol esters and the like improve the sensitivity of detection of the peroxidase enzyme in assays of the present invention by providing a larger chemiluminescence signal and a better signal to background ratio. The improvement occurs through minimizing the background chemiluminescence in the absence of added peroxidase, possibly due to a slowing of the autoxidative decomposition of the acridan derivative. The preferred amounts of the various components of a composition of the present invention are set forth below.

TABLE 1

Reagent Compositions for Producing Chemiluminescence with a Peroxidase Enzyme.

| | |
|---|---|
| Acridan | 0.01–10 mM |
| Enhancer | 0.001–10 mM |
| Surfactant | 0.005–5% |
| Peroxide | 0.01–10 mM |
| Chelating agent | 0.01–5 mM |

This solution is contacted with the peroxidase enzyme which can either be in solution or adhered to a solid support. Optimum concentrations of reagents must be determined individually for each composition. The concentration of acridan compound and enhancer in particular should be optimized with care for each case in order to produce the maximum enhancement of light emission. The detection reaction can be performed over a range of temperatures including at least the range 20–40° C. Detection can be conveniently and advantageously carried out at ambient temperature.

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, x-ray films with maximum response to either UV to blue light or green light are available. Choice of the detection device will be governed by the application and considerations of cost, convenience, and whether creation of a permanent record is required.

Another aspect of the present invention is a method for detecting a peroxidase enzyme or an analyte linked to or capable of being linked to a peroxidase enzyme in an assay procedure by a chemiluminescent reaction. The method comprises reacting an acridan of formula I with a peroxide and the peroxidase enzyme to produce chemiluminescence, detecting the amount of chemiluminescence and relating the amount of chemiluminescence to the amount of the analyte or enzyme.

The present invention also relates to a method for detecting hydrogen peroxide in an assay procedure by a chemiluminescent reaction. The method comprises reacting hydrogen peroxide and a peroxidase enzyme with an acridan of formula I to produce chemiluminescence and relating the amount of chemiluminescence to the amount of peroxide.

Further, the invention relates to the use of the method to detect and quantify various biological molecules which are bound to this enzyme by chemical bonds or through physical interactions. Further, the invention relates to the use of the method to detect and quantify various biological molecules which have been or are capable of being bound to peroxidase, for example, by using a biotin-labeled analyte and streptavidin-peroxidase conjugate. Other high affinity binding pairs well known in the art such as fluorescein and anti-fluorescein, digoxigenin and anti-digoxigenin or complementary nucleic acid sequences can also be readily employed as a means of linking a peroxidase enzyme to an analyte for the purpose of practicing this invention. The intensity of the resulting chemiluminescence provides a direct measure of the quantity of labeled organic or biological molecule. For example, the method can be used to detect haptens, antigens and antibodies by the technique of immunoassay, proteins by Western blotting, and DNA and RNA by Southern and Northern blotting, respectively. The method can also be used to detect DNA in DNA sequencing applications.

The method can additionally be used to detect hydrogen peroxide generated by enzymes such as cholesterol oxidase, glucose oxidase, glucose-6-phosphate dehydrogenase, galactose oxidase, galactose-6-phosphate dehydrogenase, and amino acid oxidase. The method can also therefore be used as a means to detect the enzymes mentioned above which generate hydrogen peroxide.

In a further embodiment the methods of the present invention can be used for the detection and measurement of enzyme inhibitors. Inhibitors can act reversibly or irreversibly by denaturing the enzyme, irreversibly binding to the enzyme, or by reversibly binding to the enzyme and competing with substrate. For example, peroxidase inhibitors include cyanide, sulfide and high concentrations of hydrogen peroxide. Further it is recognized that some substances are only inhibitory at certain concentrations and can be only partially inhibitory. In a method of detecting an enzyme inhibitor according to the present invention, a compound of formula (1) is reacted with a peroxidase and a peroxide in the presence and in the absence of the inhibitor and the results are compared to determine the presence or amount of the inhibitor. The effect of the inhibitor can decrease the light intensity, slow the rate of rise of light intensity or cause a delay period before light emission begins or any combination of these effects.

EXAMPLES

Synthesis of Acridan Derivatives. Acridancarboxylic acid derivatives 1a–q were synthesized in accordance with the methods of the present invention.

TABLE 2

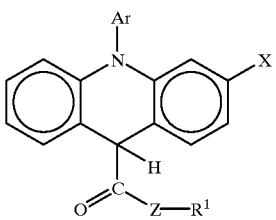

N-Arylacridancarboxylic acid derivatives Prepared.

| Compound | Ar | X | Z | $R^1$ |
|---|---|---|---|---|
| 1a | $C_6H_5$ | H | O | $C_6H_5$ |
| 1b | $C_6H_5$ | H | S | $4\text{-}Cl\text{-}C_6H_4$ |
| 1c | $C_6H_5$ | H | O | $2,3,6\text{-}C_6H_2F_3$ |
| 1d | $C_6H_5$ | H | S | $2\text{-}C_{10}H_7$ |
| 1e | $2,6\text{-}di\text{-}Me\text{-}C_6H_3$ | H | S | $4\text{-}Cl\text{-}C_6H_4$ |
| 1f | $2,6\text{-}di\text{-}Me\text{-}C_6H_3$ | H | S | $2\text{-}C_{10}H_7$ |
| 1g | $4\text{-}MeO\text{-}C_6H_4$ | H | S | $4\text{-}Cl\text{-}C_6H_4$ |
| 1h | $2\text{-}C_{10}H_7$ (naphthyl) | H | S | $4\text{-}Cl\text{-}C_6H_4$ |
| 1i | $2\text{-}C_{10}H_7$ | H | S | $2\text{-}C_{10}H_7$ |
| 1j | $4\text{-}C_6H_5\text{—}C_6H_4$ | H | S | $4\text{-}Cl\text{-}C_6H_4$ |
| 1k | $4\text{-}C_6H_5\text{—}C_6H_4$ | H | O | $2,3,6\text{-}C_6H_2F_3$ |
| 1l | $C_6H_5$ | H | S | $2,6\text{-}di\text{-}Me\text{-}C_6H_3$ |
| 1m | berzothiazol-2-yl | H | O | $2,3,6\text{-}C_6H_2F_3$ |
| 1n | berzothiazol-2-yl | H | S | $4\text{-}Cl\text{-}C_6H_4$ |
| 1o | $C_6H_5$ | H | C | $CH_3$ |
| 1p | $C_6H_5$ | $OCH_3$ | S | $4\text{-}Cl\text{-}C_6H_4$ |
| 1q | $C_6H_5$ | $OCH_3$ | O | $2,3,6\text{-}C_6H_2F_3$ |

Example 1

Compound 1a

A 1 L round bottom flask was charged with 16.80 g of lithium aluminum hydride (0.4427 mol) and 300 mL of diethyl ether. After hydrogen evolution had ceased, 25.00 g of 9(10H)-acridone (0.1281 mol) was added to the flask in portions with 300 mL toluene. The grey slurry was then purged with argon and the reaction was heated to reflux. The mixture was allowed to stir for 3 h when the resultant mixture, containing a yellow solid, was cooled to 0° C. and treated dropwise with 16.8 mL of water via addition funnel. Hydrogen evolution occured and 100 mL additional diethyl ether was added to the mixture. Once the bubbling ceased, 16.8 mL of a solution of 15% NaOH (weight %) was added dropwise to the mixture, followed by 50.4 mL of water. The resultant granular precipitate was isolated by suction filtration and washed thoroughly with 2 L of $CH_2Cl_2$. The solid was discarded and the organic filtrate was concentrated to dryness. The residue was chromatographed on silica gel with $CH_2Cl_2$ to afford 21.09 g of the acridan as a white solid (90.8%).

$^1$H-NMR: (CDCl$_3$) $\partial$4.05 (s, 2H), 5.94 (s, 1H), 6.66 (d, 2H), 6.85 (t, 2H), 7.05–7.11 (m, 4H).

18.12 g of acridan (0.10 mol), 17.30 g of bromobenzene (0.11 mol), 14.40 g of sodium t-butoxide (0.15 mol), 1.12 g of Pd(OAc)$_2$ (5 mmol), and 0.81 g of tri-t-butylphosphine (4 mmol) were taken up in 100 mL of dry toluene and this reaction mixture was allowed to stir under inert atmosphere. The exothermic reaction heated to reflux, then cooled to room temperature and was allowed to stir for 1 h. TLC analysis showed the reaction had gone to completion, so the reaction mixture was passed through a short plug of silica gel, which was subsequently washed with 1 L of $CH_2Cl_2$. The filtrate was concentrated to dryness and purified by column chromatography to afford 25.21 g of the N-phenylacridan (98.0%).

$^1$H-NMR: (CDCl$_3$) ∂4.23 (s, 2H), 6.18–6.20 (d, 2H), 6.82–6.96 (m, 4H), 7.13–7.15 (d, 2H), 7.32–7.34 (d, 2H), 7.47–7.52 (t, 1H), 7.59–7.64 (t, 2H).

A solution of N-phenylacridan (14.15 g, 55 mmol) in 200 mL of dry THF under inert atmosphere was cooled to −78° C. and 33.0 mL of 2.5 M n-butyllithium in hexanes (82.5 mmol) was added dropwise over 20 minutes. The solution was stirred at −78° C. for 30 minutes and then warmed to room temperature over 35 minutes. The reaction mixture was again cooled to −78° C. and 350 g of crushed dry ice was added causing a precipitate to form. The reaction was allowed to slowly warm to room temperature causing the reaction to become homogeneous. Stirring under argon was continued at room temperature. The resultant precipitate was collected by suction filtration. The solid was dissolved in 100 mL of water, which was acidified to pH 3 with 2N HCl and extracted with 4×200 mL of ethyl acetate. The combined organics were dried over sodium sulfate and concentrated to dryness to afford 8.72 g of crude product. The reaction mixture filtrate was also concentrated to dryness to afford a solid that was taken up in 300 mL of water. The aqueous solution was acidified, extracted with 3×200 mL of methylene chloride and the combined organics were dried over sodium sulfate and concentrated to afford a second crop of 3.44 g of N-phenylacridan-9-carboxylic acid (73.4%).

$^1$H-NMR: (CDCl$_3$) ∂5.12 (s, 1H), 6.30–6.33 (d, 2H), 6.88–6.93 (t, 2H), 7.02–7.07 (t, 2H), 7.25–7.34 (m, 4H), 7.47–7.52 (t, 1H), 7.58–7.63 (t, 2H).

To a solution of 3.00 g of the acid (9.96 mmol) in 100 mL of dry acetonitrile (MgSO$_4$) under inert atmosphere was added 2.10 g of carbonyl diimidazole (12.9 mmol). After stirring for 10 minutes, 1.41 g of phenol (14.9 mmol) was added to the reaction which was allowed to stir for 18 hours. An additional 1.05 g of carbonyl diimidazole (6.48 mmol) and 0.71 g of phenol (7.55 mmol) was added to the reaction, which was stirred 72 hours. The reaction mixture was concentrated in vacuo and the resultant brown oil was chromatographed on silica gel with 5% ethyl acetate in hexanes to afford 2.28 g of the ester (1a) as a brown oil. (60.6%).

$^1$H-NMR: (CDCl3) ∂5.37 (s, 1H), 6.34–6.37 (d, 2H), 6.92–6.96 (m, 4H), 7.04–7.10 (m, 2H), 7.14–7.19 (t, 1H), 7.26–7.52 (m, 6H), 7.58–7.63 (t, 2H).

Alternate Synthesis of 1a by Reaction with Phenyl chloroformate. 1.00 g of N-phenylacridan (3.9 mmol) in 30 mL of anhydrous THF was cooled to 0° C. under inert atmosphere and treated with a solution of 2.3 mL (3.8 mmol) of 2.5 M n-butyllithium in 10 mL of hexanes dropwise over 15 min. The resultant dark brown solution was warmed to room temperature over 15 min, followed by rapid addition of 1.46 mL of phenyl chloroformate (0.0117 mol). After 30 min, TLC analysis showed several products had formed. Additional stirring of the reaction mixture led to no further change by TLC, so the reaction mixture was concentrated in vacuo to a brown oil and separated on a column of silica gel eluted with 5–10% ethyl acetate in hexanes.

Example 2

Compound 1b

To a solution of 6.09 g of N-phenylacridan-9-carboxylic acid (20.2 mmol), prepared as described in Example 1, in 100 mL of dry acetonitrile (MgSO$_4$) under inert atmosphere was added 4.26 g of carbonyl diimidazole, CDI (26.3 mmol). After stirring for 10 min, 4.38 g of 4-chlorothiophenol (30.3 mmol) was added to the reaction which was allowed to stir for 1 h. The reaction mixture was concentrated in vacuo and the resultant brown solid was chromatographed on silica gel with 5%–20% ethyl acetate in hexanes to afford a yellow solid that was recrystallized in ethyl acetate and hexanes to afford 4.40 g of the thioester as a white solid. (55.3%).

$^1$H-NMR: (CDCl$_3$) ∂5.30 (s, 1H), 6.35–6.38 (d, 2H), 6.93–6.98 (t, 2H), 7.08–7.13 (t, 2H), 7.19–7.22 (d, 2H), 7.29–7.34 (m, 4H), 7.38–7.41 (d, 2H), 7.50–7.55 (t, 1H), 7.61–7.66 (t, 2H).

Example 3

Compound 1c

A solution of N-phenylacridan-9-carboxylic acid (0.36 g, 1.2 mmol) and 252 mg of CDI (1.55 mmol) was prepared in 30 mL of dry acetonitrile under inert atmosphere. After stirring for 15 min, 265.4 mg of 2,3,6-trifluorophenol (1.8 mmol) was added and stirring continued for 1 h. The reaction mixture was concentrated in vacuo and the crude product was chromatographed on a column of silica gel with 5% ethyl acetate in hexanes to afford 171.3 mg of the ester product as an oily residue. (39.7%).

$^1$H-NMR: (CDCl$_3$) ∂5.51 (s, 1H), 6.34–6.37 (d, 2H), 6.81–6.89 (m, 1H), 6.93–7.00 (m, 3H), 7.06–7.11 (m, 2H), 7.34–7.41 (m, 4H), 7.48–7.53 (t, 1H), 7.59–7.64 (t, 2H).

Example 4

Compound 1d

A solution of 3.00 g of N-phenylacridan-9-carboxylic acid (10 mmol) and 2.10 g of CDI (12.9 mmol) was prepared in 100 mL of dry acetonitrile under inert atmosphere. After stirring for 10 min, 2.39 g of 2-naphthalenethiol (14.9 mmol) was added to the reaction and the solution was allowed to stir for 1 h. TLC analysis showed product had formed, so the reaction mixture was filtered and the filtrate was concentrated in vacuo to afford a gummy brown solid. The solid was resuspended in diethyl ether, filtered and purified by column chromatography, eluting with 25–100% CH$_2$Cl$_2$ in hexanes to afford 2.16 g of pure thioester product as a white solid. (48.9%).

$^1$H-NMR: (CDCl$_3$) ∂5.34 (s, 1H), 6.37–6.39 (d, 2H), 6.94–6.99 (t, 2H), 7.09–7.14 (t, 2H), 7.291–7.33 (d, 1H), 7.36–7.55 (m, 7H), 7.61–7.66 (t, 2H), 7.74–7.83 (m, 4H).

Example 5

Compound 1e

A mixture containing 5.0 g of acridan (0.027 mol), 186 mg of Pd(OAc)$_2$ (8.2×10$^{-4}$ mol), 186 mg of tri-t-butylphosphine (8.2×10$^{-4}$ mol), 3.97 g of sodium t-butoxide (0.041 mol), and 6.12 g of 1-bromo-2,6-dimethylbenzene (0.033 mol) in 70 mL of dry toluene was stirred under argon at room temperature for 16 h. Since TLC analysis still showed the presence of starting material, the reaction mixture was heated at 85° C. for 3 h. The reaction mixture was cooled, filtered and the precipitate was washed with diethyl ether. The filtrate was passed through a 2" plug of celite and concentrated to a brown solid. The crude product was chromatographed on silica gel with 5%–20% CH$_2$Cl$_2$ in hexanes to afford 5.1 g (66.2%) of N-(2,6-dimethylphenyl)acridan.

$^1$H-NMR: (CDCl$_3$) ∂2.06 (s, 6H), 4.32 (s, 2H), 6.01–6.03 (d, 2H), 6.81–7.29 (m, 10H).

A solution of 4.28 g of N-(2,6-dimethylphenyl)acridan (15 mmol) in 100 mL of THF under argon was cooled to −78° C. After 10 min, 7.6 mL of n-BuLi (18.7 mmol) was added. The black solution stirred 30 min and then the temperature was raised to 0° C. for 40 min. The reaction was again cooled to −78° C. and 270 g of crushed dry ice was added to the reaction mixture to form a yellow solution with a white precipitate that dissolved once the reaction was warmed to room temperature. The reaction was stirred for 16 h at room temperature, and then concentrated and taken up in a mixture of water and diethyl ether. The aqueous portion was acidified with HCl to afford a white precipitate, which was filtered and dried to give 4.8 g of N-(2,6-dimethylphenyl)acridan-9-carboxylic acid as a white solid (97%).

$^1$H-NMR: (DMSO-$d_6$) $\partial$1.83 (s, 3H), 2.03 (s, 3H), 5.12 (s, 1H), 5.98–6.01 (d, 2H), 6.87–7.37 (m, 10H), 12.47 (bs, 1H).

A solution of the preceding acid (6.1 mmol) and 1.03 g of CDI (6.4 mmol) in 30 mL of THF was stirred for 10 min under inert atmosphere when 1.1 g of p-chlorothiophenol (7.6 mmol) was added to the reaction mixture. After 20 min, the reaction mixture was chromatographed on silica gel in 5%–40% $CH_2Cl_2$ in hexanes to afford 2.1 g of white solid (75.5%). $^1$H-NMR analysis confirmed the white solid as the desired thioester.

$^1$H-NMR: ($CDCl_3$) $\partial$1.92 (s, 3H), 2.22 (s, 3H), 5.37 (s,1H), 6.16–6.19 (d, 2H),6.92–7.37 (m, 13H).

Example 6

Compound 1f

A solution of 2.0 g of N-(2,6-dimethylphenyl)-acridan-9-carboxylic acid (6.1 mmol) prepared as described in Example 5, and 1.03 g of CDI (6.4 mmol) in 30 mL of THF was stirred for 10 min under inert atmosphere when 1.21 g of 2-naphthalenethiol (7.6 mmol) was added to the reaction mixture. The reaction was stirred at room temperature for 2 h. The reaction mixture was then chromatographed on silica gel with 30% $CH_2Cl_2$ in hexanes to afford 1.4 g of the desired thioester (49%).

$^1$H-NMR: ($CDCl_3$) $\partial$1.94 (s, 3H), 2.26 (s, (3H), 5.42 (s, 1H), 6.17–6.20 (d, 2H), 6.94–6.99 (t, 2H), 7.09–7.15 (t, 2H), 7.26–7.49 (m, 8H), 7.74–7.82 (m, 4H).

Example 7

Compound 1g

A mixture of 10.00 g of acridan (55.2 mmol), 0.260 g of Pd(OAc)$_2$ (1.16 mmol), 0.223 g of tri-t-butylphosphine (1.1 mol), 8.75 g of sodium t-butoxide (91 mmol), and 6.90 mL of bromoanisole (60.7 mmol) in 55 mL of dry toluene was purged with argon and the black solution was allowed to stir at room temperature. After 10 min, 20 mL additional toluene was added to the thick solution and the reaction was allowed to stir for 1 h. The reaction mixture was filtered and the collected precipitate was washed with 50 mL of $CH_2Cl_2$, followed by 50 mL of THF. The precipitate was then triturated in water for 1 h, collected by suction filtration, and allowed to air dry. NMR analysis showed 11.5 g of N-(4-methoxyphenyl)acridan was isolated in pure form (72.5%).

$^1$H-NMR: ($CDCl_3$) $\partial$3.90 (s, 3H), 4.22 (s, 2H), 6.23 (d, 2H), 6.84 (t, 2H), 6.95 (t, 2H), 7.12 (m, 4H), 7.24 (d, 2H).

N-(4-Methoxyphenyl)acridan (9.23 g, 32.1 mmol) in 220 mL of dry THF was cooled to −78° C. under inert atmosphere and treated dropwise with a solution of 20 mL of 2.5 M n-butyllithium (48.2 mmol). The reaction mixture was warmed to room temperature to afford a dark brown solution which was stirred for 20 min. The reaction was again cooled to −78° C., and 350 g of dry ice was added to the solution. The reaction was warmed to room temperature and was stirred for 12 h. The resultant slurry was separated by suction filtration, and the s solid was w ash ed with 30 mL of THF and dissolved in 300 mL of H2O. The aqueous solution was acidified to pH 2 and a dark oil separated out of the milky white solution. The solution was decanted, extracted with 3×100 mL of ethyl acetate, and the combined organics were dried over sodium sulfate and concentrated to dryness to afford 1.8 g of the desired product. The dark oil was extracted into ethyl acetate and the organic layer was dried over sodium sulfate and concentrated to dryness to afford 5.95 g of a solid containing 1:1 carboxylic acid product:impurity. Total yield: 7.75 g.

$^1$H-NMR: ($CDCl_3$) $\partial$3.90 (s, 3H), 5.11 (s, 1H), 6.35 (d, 2H), 6.91 (t, 2H), 7.05 (t, 2H), 7.10 (d, 2H), 7.24 (d, 4H).

To a solution of 0.92 g of the acid (2.78 mmol) in 20 mL of dry THF under inert atmosphere was added 0.59 g of CDI (3.62 mmol). After stirring for 10 min, 0.60 g of 4-chlorothiophenol (4.18 mol) was added to the reaction which was allowed to stir for 3 h. The reaction mixture was chromatographed on silica gel with 5% ethyl acetate in hexanes to afford 310 mg of the thioester. (24%).

$^1$H-NMR: ($CDCl_3$) $\partial$3.89 (s, 3H), 5.28 (s, 1H), 6.40 (d, 2H), 6.93 (t, 2H), 7.07–7.13 (m, 4H), 7.18 (d, 2H), 7.26–7.32 (m, 6H).

Example 8

Compound 1h 10.02 g of acridan (55.3 mmol), 12.67 g of 2-bromonaphthalene (61.2 mmol), 8.02 g of sodium t-butoxide (83.5 mmol), 0.25 g of Pd(OAc)$_2$ (1.11 mmol), and 0.19 g of tri-t-butylphosphine (0.94 mmol) were taken up in 100 mL of dry toluene and the reaction mixture was allowed to stir for 18 h under inert atmosphere. TLC and NMR analysis showed starting material present, so 0.19 g of tri-t-butylphosphine (0.94 mol) and Pd(OAc)$_2$ were added to the reaction mixture, causing an exothermic reaction that warmed the reaction mixture above room temperature. After stirring an additional 2 h, TLC analysis showed the reaction had gone to completion. The reaction mixture was concentrated to a black oil and chromatographed on silica gel with 4% ethyl acetate in hexanes to afford 14.02 g of a white solid. NMR analysis confirmed the desired N-(2-naphthyl) acridan was isolated in 82.6% yield.

$^1$H-NMR: ($CDCl_3$) $\partial$4.27 (s, 2H), 6.22 (d, 2H), 6.82–6.94 (m, 4H), 7.17 (d, 2H), 7.39 (dd, 1H), 7.52–7.64 (m, 2H), 7.87–7.90 (m, 2H), 7.97 (d, 1H), 8.10 (d, 1H).

N-(2-naphthyl)acridan (9.00 g, 29.3 mmol) in 200 mL of dry THF was cooled to −78° C. under inert atmosphere and 18 mL of 2.5 M n-BuLi in hexanes (45 mmol) was added. The solution was stirred at −78° C. for 30 min and then warmed to room temperature. The reaction mixture was added to a esparate, stoppered flask containing solid CO2 via syringe and was allowed to slowly warm to room temperature. The reaction mixture was then concentrated in vacuo to afford a yellow solid which was washed with the acetone to remove impurities. The remaining white solids were dissolved in water, acidified to pH 2–3 and extracted with ethyl acetate. The combined organics were dried over magnesium sulfate and concentrated to a brown gummy solid (8.21). NMR analysis showed the solid contained both the desired acid and scme impurity. This product was taken directly to the esterification reaction without further purification.

To a solution of crude N-(2-naphthyl)acridan-9-carboxylic acid (8.21 g , ca. 23.4 mmol) in 80 mL of dry DMF under inert atmosphere was added 5.31 g of CDI (32.7 mmol). After stirring for 15 min, 5.41 g of 4-chlorothiophenol (37.4 mmol) was added to the reaction which was allowed to stir for 18 h. The reaction mixture was concentrated in vacuo and chromatographed on silica gel with 3% ethyl acetate in hexanes to afford an impure, off-white solid (6.57 g). This solid was purified again by column chromatography (silica gel, 2% ethyl acetate in hexanes) to afford 4.12 g of a solid containing 20–25% of the desired product by NMR analysis, and 0.96 g of a solid containing 75–80% of the desired product by NMR analysis. Each of these solids were rechromatographed in 5% ethyl acetate in hexanes to afford a combined amount of 1.04 g of the desired ester as a white solid (24.4% over two steps).

¹H-NMR: (CDCl3) ∂5.34 (s, 1H), 6.39 (d, 2H), 6.92–7.00 (m, 2H), 7.03–7.12 (m, 2H), 7.23–7.26 (m, 1H), 7.30–7.40 (m, 4H), 7.45 (dd, 1H), 7.54–7.66 (m, 2H), 7.88–7.93 (m, 2H), 7.99 (d, 1H), 8.12 (d, 1H).

Example 9

Compound 1i

N-(2-naphthyl)acridan-9-carboxylic acid (8.04 g , ca. 22.9 mmol) prepared as described in Example 8 in 50 mL of dry DMF under inert atmosphere was added 4.89 g of CDI (30.1 mmol). After stirring for 5 minutes, 5.69 g of 2-naphthalenethiol (35.5 mmol) was a added to the reaction which was allowed to stir for 18 hours. The reaction mixture was concentrated in vacuo and the residue was taken up in $CH_2Cl_2$ and extracted with water. The material obtained from the extracted $CH_2C_2$ was chromatographed on silica gel with 10% ethyl acetate in hexanes to afford a crude solid (5.85 g). This solid was purified again by column chromatography (silica gel, 5% ethyl acetate in hexanes) to afford a combined total of 4.40 g of slightly impure product (~65%). One of the fractions containing 1.07 g of material was ~90% pure by NMR analysis. ¹H-NMR: (CDCl₃) ∂5.38 (s, 1H), 6.40–6.42 (d, 2H), 6.96–7.00 (t, 2H), 7.06–7.12 (t, 2H), 7.33–7.61 (m, 8H), 7.76–7.80 (m, 7H) 8.07–8.13 (m, 1H)

Example 10

Compound 1j 10.00 g of acridan (55.2 mmol), 14.15 g of 4-bromobiphenyl (60.7 mmol), 7.95 g of sodium t-butoxide (82.7 mmol), 0.25 g of Pd(OAc)₂ (1.10 mmol), and 0.18 g of tri-t-butylphosphine (0.88 mmol) were taken up in 50 mL of dry toluene and this reaction mixture was allowed to stir under inert atmosphere for 1 h. TLC analysis showed the reaction had gone to completion, so 300 mL of $CH_2Cl_2$ and 100 g of silica gel were added to the reaction mixture. This mixture was stirred and filtered, and the solid material was washed with an addition 1.5 L of $CH_2Cl_2$. The filtrate was concentrated in vacuo to afford a thick liquid containing a precipitate. The precipitate was collected by filtration, washed with hexanes, and dried to afford 13.09 g of the desired product by ¹H-NMR analysis. The mother liquor was concentrated to a yellow solid which was triturated in hexanes. The solid was collected by filtration to afford a second crop of product. The filtrate was again concentrated, triturated with hexanes and filtered to afford a third crop of product containing ~10% impurity by ¹H-NMR analysis. The three lots of product were combined to afford 18.60 g of N-biphenylacridan.

¹H-NMR: (CDCl₃) ∂4.25 (s, 2H), 6.28–6.31 (d, 2H), 6.84–6.89 (t, 2H), 6.95–6.99 (t, 2H), 7.15–7.17 (d, 2H), 7.38–7.43 (m, 3H), 7.48–7.53 (t, 2H), 7.68–7.71 (d, 2H), 7.82–7.85 (d, 2H).

N-biphenylacridan (13.09 g, 39 mmol) was dissolved in 200 mL of dry THF under inert atmosphere. The solution was cooled to −78° C. and 23.6 mL of 2.5 M n-BuLi in hexanes (59 mmol) was added dropwise over 15 min. The solution was stirred at −78° C. for 30 min and then warmed to room temperature over 30 min. The reaction mixture was again cooled to −78° C. and 400 g of crushed dry ice was added, causing a precipitate to form. The reaction was allowed to slowly warm to room temperature causing the reaction to become homogeneous. Stirring under argon was continued at room temperature and the reaction mixture again developed a precipitate. After stirring 18 h, the precipitate was collected by suction filtration and washed with 300 mL of diethyl ether. The solid was stirred in 500 mL of water, which was then treated with 50 mL of 15% NaOH (aq), but a homogeneous solution was not obtained. The mixture was acidified to pH 3 with 2N hydrochloric acid and extracted with 3×800 mL of ethyl acetate. The combined organics were dried over sodium sulfate and concentrated to dryness to afford a light yellow solid. This solid was triturated in hexanes, filtered and dried to afford 5.79 g of the carboxylic acid. The filtrate from the hexanes wash was also concentrated to dryness to afford a second crop of product. Total yield was 10.97 g (74.0%).

¹H-NMR: (CDCl₃) ∂5.06 (s, 1H), 6.37–6.39 (d, 2H), 6.88–6.90 (m, 2H), 7.01–7.03 (m, 2H), 7.28–7.30 (m, 2H), 7.38–7.40 (m, 3H), 7.46–7.48 (m, 2H), 7.67–7.69 (m, 2H), 7.80–7.83 (m, 2H).

To a solution of 2.20 g of the acid (5.8 mmol) in 100 mL of dry THF (MgSO₄) under inert atmosphere was added 1.23 g of CDI (7.6 mmol). After stirring for 15 min, 1.26 g of 4-chlorothiophenol (8.7 mmol) was added to the reaction which was allowed to stir for 18 h. The reaction mixture was concentrated in vacuo and the resultant brown oil was chromatographed on silica gel with 5% ethyl acetate in hexanes to afford 1.90 g (64.6%)of the thioester as a white solid.

¹H-NMR: (CDCl₃) ∂5.32 (s, 1H), 6.45–6.48 (d, 2H), 6.95–6.99 (t, 2H), 7.11–7.16 (t, 2H), 7.20–7.23 (d, 2H), 7.29–7.36 (m, 4H), 7.42–7.53 (m, 5H), 7.68–7.71 (d, 2H), 7.83–7.86 (d, 2H).

Example 11

Compound 1k

A solution of N-biphenylacridan-9-carboxylic acid (1.50 g, 4 mmol) as prepared in Example 10 in 100 mL of dry THF (MgSO₄) under inert atmosphere was treated with 0.84 g of CDI (5.2 mmol). After stirring for 15 min, 0.89 g of 2,3,6-trifluorophenol (6 mmol) was added to the reaction which was allowed to stir for 90 h. The reaction mixture was concentrates. in vacuo and the resultant brown residue was chromatographed on silica gel with 5%–10% ethyl acetate in hexanes to afford a white solid. The impure product was again chromatographed on silica gel with 50% $CH_2Cl_2$ in hexanes to afford 1.30 g (64.7%) of the ester as a white solid.

¹H-NMR: (CDCl₃) ∂5.53 (s, 1H), 6.45–6.48 (d, 2H), 6.81–6.89 (m, 1H), 6.94–7.05 (m, 3H), 7.09–7.15 (t, 2H), 7.38–7.53 (m, 7H), 7.68–7.70 (d, 2H), 7.82–7.84 (d, 2H).

Example 12

Compound 1l

A solution of 8.00 g of N-phenylacridan-9-carboxylic acid (26.6 mmol) and 5.60 g of CDI (34.5 mmol) in 300 mL of dry CH3CN (MgSO4) was stirred under inert atmosphere for 1 h. 2,6-dimethylthiophenol (5.50 g, 39.8 mmol) was added to the reaction which was allowed to stir for 18 h. The reaction mixture was concentrated in vacuo and the resultant brown solid was chromatographed on silica gel with 5% ethyl acetate in hexanes to afford 6.49 g of 2',6'-dimethylthiophenyl 10-phenylacridan-9-carboxylate (58%).

¹H-NMR: (CDCl3) ∂2.09 (s, 6H), 5.31 (1H), 6.33–6.36 (d, 2H), 6.90–6.95 (t, 2H), 7.04–7.17 (m, 5H), 7.32–7.34 (d, 2H), 7.39–7.41 (d, 2H), 7.49–7.54 (t, 1H), 7.60–7.65 (t, 2H).

Example 13

Compound 1m

A mixture of 16.2 g of acridan (89.2 mmol), 1.00 g of Pd(OAc)₂ (4.46 mmol), 0.72 g of tri-t-butylphosphine (3.56 mmol), 12.9 g of sodium t-butoxide (134 mmol), and 16.6 g of 2-chlorobenzothiazole (98.1 mmol) in 200 mL of dry toluene was allowed to stir under inert atmosphere at room temperature for 72 h. The reaction mixture was poured into a mixture of 300 mL of $CH_2Cl_2$ and 100 g of silica gel. The mixture was filtered, washed with an additional 1 L of $CH_2Cl_2$, and the solids were discarded. The filtrate was concentrated in vacuo to afford a brown solid. The solid was triturated in 2×200 mL of hexanes, filtered, washed with an additional 100 mL of hexanes, and dried to afford a light brown solid containing 2:1 desired product:starting arterial by NMR analysis. The solid was taken up in 500 mL of $CH_2C_2$ and treated with 7.8 mL of oxalyl chloride (89.4 mmol) to convert the starting material to a more polar derivative to facilitate separation. The mixture stirred 6 h and the resultant precipitate was collected by fitration, washed with 100 mL $CH_2Cl_2$, and analysed by NMR to show the pure HCl salt of N-benzothiazolylacridan was obtained. This solid was treated with 7.5 mL triethylamine in 500 mL $CH_2Cl_2$. After stirring 1 h, the mixture was washed with 3×400 mL of water, dried over sodium sulfate, and concentrated to afford 11.47 g of a yellow solid. NMR analysis confirmed the solid was the pure N-benzothiazolylacridan (41%).

$^1$H-NMR: ($CDCl_3$) ∂3.91 (s, 2H), 7.16–7.23 (m, 3H), 7.30–7.37 (m, 5H), 7.60–7.63 (d, 1H), 7.70–7.73 (d, 1H), 7.95–7.98 (d, 2H).

N-benzothiazolylacridan (11.47 g, 36.5 mmol) was dissolved in 500 mL of dry THF under inert atmosphere. The solution was cooled to −78° C. and 21.9 mL of 2.5 M n-BuLi in hexanes (54.7 mmol) was added dropwise over 15 minutes. The solution was stirred at −78° C. for 30 min and then warmed to room temperature over 30 min. The reaction mixture was again cooled to −78° C. and 300 g of crushed dry ice was added. The reaction was allowed to slowly warm to room temperature. After stirring 18 h, the reaction mixture was concentrated in vacuo. The residue was dissolved in 300 mL of water, acidified to pH 6 with concentrated HCl. After stirring 15 min, the resultant precipitate was collected by filtration, washed with 100 mL water, and dried to afford 8.93 g of solid. The filtrate was acidified to pH 3 with concentrated HCl and formed a precipitate while stirring at room temperature. The precipitate was collected by filtration and dried to afford 2.65 g of solid. NMR analysis of both crops confirmed N-benzothiazolylacridan-9-carboxylic acid had been isolated (11.58 g, 89%).

$^1$H-NMR: (CDCl3) ∂4.82 (s, 1H), 7.17–7.26 (m, 3H), 7.32–7.43 (m, 5H), 7.62–7.70 (m, 2H), 7.94–7.96 (d, 2H).

A solution of 2.00 g of the acid (5.58 mmol) and 1.18 g of CDI (7.25 mmol) in 100 mL of dry THF was stirred under inert atmosphere for 15 min. 1.24 g of 2,3,6-trifluoro-phenol (8.37 mmol) was added to the reaction which was allowed to stir for 18 h. The reaction mixture was concentrated in vacuo and the resultant yellow oil was chromatographed twice (silica gel, 5% ethyl acetate in hexanes and 50% $CH_2Cl_2$ in hexanes) to afford 0.63 g of a white solid (23%). $^1$H-NMR analysis confirmed isolation of 2',3',6'-trifluorophenyl 10-benzothiazolylacridan-9-carboxylate.

$^1$H-NMR: (CDCl3) ∂5.29 (s, 1H), 6.71–6.80 (m, 1H), 6.86–6.97 (m, 1H), 7.24–7.28 (m, 3H), 7.38–7.43 (t, 3H), 7.48–7.51 (d, 2H), 7.64–7.67 (d, 1H), 7.84–7.93 (m, 3H).

Example 14

Compound 1n

A solution of 4.00 g of N-benzothiazolylacridan-9-carboxylic acid (11.2 mmol) and 2.35 g of CDI (14.5 mmol) in 250 mL of dry THF was stirred under inert atmosphere for 15 min. 2.42 g of p-chlorothiophenol (16.7 mmol) was added to the reaction which was allowed to stir for 18 h. The reaction mixture was concentrated in vacuo and the resultant yellow oil was chromatographed on silica gel with 50% $CH_2Cl_2$ in hexanes to afford 2.45 g of a white solid (45%). $^1$H-NMR analysis confirmed isolation of 4'-chlorothiophenyl 10-benzothiazolylacridan-9-carboxylate.

$^1$H-NMR: (CDCl3) ∂5.07 (s, 1H), 7.02–7.05 (d, 2H), 7.18 7.21 (d, 2H), 7.23–7.30 (m, 3H), 7.39–7.45 (m, 5H), 7.67–7.70 (d, 1H), 7.85–7.93 (m, 3H).

Example 15

Compound 1o

A solution of 1.00 g of acridan-9-carboxylic acid methyl ester (4.18 mmol), 0.44 mL of bromobenzene (4.18 mmol), 0.60 g of sodium t-butoxide (6.27 mmol), 23 mg of Pd(OAc)$_2$ (0.105 mmol), and 17 mg of tri-t-butylphosphine (0.084 mmol) in 15 mL of toluene was stirred under inert atmosphere at room temperature. After 2.5 h, 5 g of silica gel in 15 mL of $CH_2Cl_2$ was added to the reaction mixture. The slurry was filtered, washed with excess $CH_2Cl_2$ and the filtrate was concentrated to a thick solution. 20 mL of hexanes was added to this solution, causing a white precipitate to form. The precipitate was filtered, washed with hexanes, and dried to afford 0.96 g of N-phenylacridan-9-carboxylic acid methyl ester (72%).

$^1$H-NMR: (CDCl3) ∂3.66 (s, 3H), 5.17 (s, 1H), 6.30–6.33 (d, 2H), 6.89 (t, 2H), 7.04 (t, 2H), 7.25–7.27 (m, 2H), 7.34–7.36 (d, 2H), 7.50 (t, 1H), 7.59–7.62 (t, 2H).

Example 16

Compound 1p

A solution of 60.0 g of o-chlorobenzoic acid (0.38 mol), 60.0 g of potassium carbonate (0.43 mol), 49.8 g of m-anisidine (0.40 mol), and 1.98 g of copper powder (0.031 mol) in 600 mL of pentanol was stirred at reflux for 27 h. The reaction mixture was concentrated in vacuo to afford a black solid. The solid was dissolved in 600 mL of water and poured into 3 L of water containing 300 mL of concentrated HCl. The resultant black precipitate was collected by filtration, washed with 2 L of water and dried to afford 91.25 g of solid N-(2-carboxyphenyl)anisidine (98%).

$^1$H-NMR: ($CD_3OCD_3$) ∂3.80 (s, 3H), 6.65–6.68 (d, 1H), 6.78–6.86 (m, 3H), 7.21–7.44 (m, 3H), 8.01–8.04 (d, 1H), 9.6 (s, 1H).

An solution of 90.25 g of the acid (0.37 mol) in 250 mL of $POCl_3$ (exothermic) was stirred for several minutes, then heated to reflux and allowed to stir 6 h. The reaction mixture was cooled to room temperature and concentrated in vacuo. The brown residue was dissolved in 1 L of $CH_2Cl_2$. A 2 L solution of 5% $NH_4OH$ in water was slowly added with rapid stirring. Once the mixture stopped bubbling, the organic layer was separated, dried over sodium sulfate, and concentrated to a dark brown solid. The solid was triturated in 1 L of hexanes, collected by filtration, and dried to afford 94.34 g of a yellow/brown solid 3-methoxy-9-chloroacridine (104%).

$^1$H-NMR: (CDCl3) ∂4.02 (s, 3H), 7.29–7.33 (d, 1H), 7.44–7.45 (s, 1H), 7.56–7.61 (m, 1H), 7.77–7.82 (t, 1H), 8.14–8.17 (d, 1H), 8.30–8.33 (d, 1H), 8.38–8.41 (d, 1H).

A solution of 93.34 g of 3-methoxy-9-chloroacridine (0.38 mol) in 2 L of 5 N HCl was stirred at reflux for 40 h. The reaction mixture was cooled to room temperature and the precipitate was collected by suction filtration, washed with 1 L of water, and dried. The solid was stirred in 1 L of methanol and the insoluble precipitate was collected by filtration to afford 15.3 g of the desired 3-methoxy-acridine. The filtrate was concentrated in vacuo and chromatographed on silica gel in 20% methanol in $CH_2Cl_2$ to afford a dark brown solid. The solid was triturated in 200 mL of methanol and the insoluble precipitate was collected by filtration to afford a second crop of product. The filtrate was concentrated to a thick solution, and a third crop of product was collected by filtration. The second and third crop of product were combined to give 2.6 g of 3-methoxyacridone, for a combined total of 17.9 g (21%).

¹H-NMR: (CDCl3) ∂3.93 (s, 3H), 6.80–6.87 (m, 2H), 7.18–7.23 (t, 1H), 7.43–7.46 (d, 1H), 7.58–7.64 (t, 1H), 8.28–8.31 (d, 1H), 8.35–8.38 (d, 1H), 11.0 (s, 1H).

To a stirred solution of 15.29 g of 3-methoxyacridone (67.9 mmol) in 200 mL of diethyl ether was added 7.73 g of LiAlH$_4$ slowly portionwise. Once evolution of H$_2$ ceased, 200 mL of dry toluene was added under inert atmosphere and the reaction was stirred at reflux for 2 h. The reaction mixture was cooled to 0° C. and dropwise addition of 8.0 mL of water, 8.0 mL of 15% NaOH (aq) and 24.0 mL of water were performed sequentially. 500 mL of CH$_2$Cl$_2$ was added and the resultant precipitate was filtered, washed with 500 mL of CH$_2$Cl$_2$ and discarded. The filtrate was concentrated in vacuo, resuspended in hexanes, and again concentrated to afford 14.06 g of 3-methoxyacridan (98%).

¹H-NMR: (CDCl3) ∂3.77 (s, 3H), 4.00 (s, 2H), 5.94 (bs, 1H), 6.23 (s, 1H), 6.41–6.44 (d, 1H), 6.63–6.66 (d, 1H), 6.82–6.87 (t, 1H), 6.98–7.10 (m, 3H).

A mixture of 13.0 g of 3-methoxyacridan (57.7 mmol), 259 mg of Pd(OAc)$_2$ (1.15 mmol), 187 g of tri-t-butylphosphine (0.92 mmol), 8.32 g of sodium t-butoxide (86.6 mmol), and 10.9 g of bromobenzene (69.2 mmol) in 100 mL of dry toluene was stirred under inert atmosphere at room temperature for 18 h. The reaction mixture was poured into a mixture of 300 mL of CH$_2$Cl$_2$ and 100 g of silica gel. The mixture was filtered, washed with an additional 500 mL of CH$_2$Cl$_2$, and the solids were discarded. The filtrate was concentrated in vacuo to afford a yellow solid. The solid was triturated in 100 mL of hexanes, filtered, washed with an additional 100 mL of hexanes, and dried to afford 13.8 g of N-phenyl-3-methoxyacridan, by NMR analysis (83%).

¹H-NMR: (CDCl3) ∂3.62 (s, 3H), 4.17 (s, 2H), 5.77 (s, 1H), 6.16–6.18 (d, 1H), 6.40–6.43 (d, 1H), 6.82–6.86 (t, 1H), 6.90–6.95 (t, 1H), 7.03–7.06 (d, 1H), 7.12–7.14 (d, 1H), 7.30–7.33 (d, 2H), 7.45–7.50 (t, 1H), 7.57–7.62 (t, 2H).

N-phenyl-3-methoxyacridan (12.5 g, 43.5 mmol) was dissolved in 500 mL of dry THF under inert atmosphere. The solution was cooled to −78° C. and 26.1 mL of 2.5 M n-BuLi in hexanes (65.3 mmol) was added dropwise over 15 min. The solution was stirred at −78° C. for 30 min and then warmed to room temperature. The reaction mixture was again cooled to −78° C. and 300 g of crushed dry ice was added. The reaction was allowed to slowly warm to room temperature. After stirring 18 h, the reaction mixture was concentrated in vacuo. The residue was dissolved in 300 mL of water, acidified to pH 6 with concentrated HCl, and allowed to stir 15 min. The resultant precipitate was collected by filtration, washed with 100 mL water, and dried to afford 2.91 g of product, by NMR analysis. The filtrate was acidified to pH 4 with concentrated HCl and formed a precipitate while stirring at room temperature. The precipitate was collected by filtration, washed with 100 mL of water and dried to afford a second crop of product. A third and fourth crop of product were isolated by acidifying and filtering in the same manner, to afford a total of 10.97 g of product. NMR analysis of each crop confirmed the crude acid had been isolated (13.9 g, 96%).

¹H-NMR: (DMSO-d) ∂3.54 (s, 3H), 4.92 (s, 1H), 5.64 (s, 1H), 6.13–6.15 (d, 1H), 6.46–6.49 (d, 1H), 6.82–6.87 (t, 1H), 6.97–7.01 (t, 1H), 7.15–7.18 (d, 1H), 7.22–7.24 (d, 1H), 7.30–7.35 (d, 2H), 7.54–7.59 (t, 1H), 7.66–7.71 (t, 2H).

A solution of 4.00 g of 3-methoxy-10-phenylacridan-9-carboxylic acid (12.1 mmol) and 2.54 g of CDI (15.7 mmol) in 200 mL of dry THF was stirred under inert atmosphere for 15 min. 2.62 g of 4-chlorothiophenol (18.1 mmol) was added to the reaction which was allowed to stir for 18 h. The reaction mixture was concentrated in vacuo and the resultant brown oil was chromatographed on silica gel in 50% CH$_2$Cl$_2$ in hexanes to afford 4.06 g of a gummy white solid (73%). ¹H-NMR analysis confirmed isolation of 4'-chlorothicphenyl 3-methoxy-10-phenylacridan-9-carboxylate.

¹H-NMR: (CDCl3) ∂3.66 (s, 3H), 5.24 (s, 1H), 5.90 (s, 1H), 6.32–6.35 (d, 1H), 6.51–6.54 (d, 1H), 6.91–6.96 (t, 1H), 7.06–7.12 (t, 1H), 7.19–7.33 (m, 6H), 7.37–7.40 (d, 2H), 7.49–7.54 (t, 1H), 7.60–7.65 (t, 2H).

Example 17

Compound 1q

A solution of 2.00 g of 3-methoxy-10-phenylacridan-9-carboxylic acid (6.04 mmol) and 1.27 g of CDI (7.85 mmol) in 100 mL of dry THF was stirred under inert atmosphere for 15 min. 1.34 g of 2,3,6-trifluorophenol (9.05 mmol) was added to the reaction which was allowed to stir for 18 h. The reaction mixture was concentrated in vacuo and the resultant brown oil was chromatographed on silica gel with 50% CH$_2$Cl$_2$ in hexanes to afford a yellow liquid. The liquid was stirred in diethyl ether and concentrated in vacuo three times to afford a brown solid. The solid was triturated in 25 mL of diethyl ether, collected by filtration, and dried to afford 578 mg of 2',3',6'-trifluorophenyl 3-methoxy-10-phenylacridan-9-carboxylate.

¹H-NMR: (CDCl3) ∂3.64 (s, 3H), 5.46 (s, 1H), 5.90 (s, 1H), 6.32–6.35 (d, 1H), 6.51–6.54 (d, 1H), 6.80–6.88 (m, 1H), 6.92–7.10 (m, 3H), 7.30–7.39 (m, 4H). 7.47–7.52 (t, 1H), 7.57–7.62 (t, 2H).

Synthesis of Acridans. The following additional N-arylacridans (3) were synthesized by Pd-catalyzed coupling of acridan and an aromatic compound in accordance with the methods of the present invention and can be converted to N-arylacridencarboxylic acids and acid derivatives (1) in accordance with the methods of the present invention.

TABLE 3

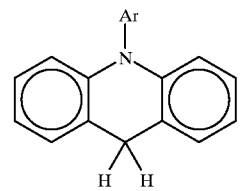

Additional N-Arylacridans Synthesized
Ar

4-PivO-C$_6$H$_4$
4-NO$_2$-C$_6$H$_4$
3-PivO-C$_6$H$_4$
3-HO-C$_6$H$_4$
4-F-C$_6$H$_4$
4-(Benzothiazol-2-yl)-phenyl
anthryl
2-pyrenyl
4-CN-C$_6$H$_4$
4-PivO-C$_6$H$_4$-C$_6$H$_4$
2-C$_6$H$_4$N (pyridyl)

Example 18

Synthesis of N-(4'-pivaloyloxyphenyl)acridan

A solution of 20.02 g of 4-bromophenol (0.116 mol) in 100 mL of dry THF was treated with 15.0 mL of pivaloyl chloride (0.126 mol), followed by 35.5 mL of triethylamine (0.255 mol). A large amount of white solid precipitated so 50 mL of additional THF was added to the mixture to afford a free-flowing slurry. The reaction mixture was filtered and the precipitate was washed with 200 mL THF and then discarded. The filtrate was concentrated in vacuo to a liquid which solidified when dried under reduced pressure to yield 30.5 g (100%) of 4-bromophenyl pivalate.

$^1$H-NMR: (CDCl$_3$) ∂1.35 (s, 9H), 6.95 (d, 2H), 7.81 (d, 2H).

A mixture of 7.05 g of acridan (38.9 mmol), 0.218 g of Pd(OAc)$_2$ (0.97 mmol), 0.157 g of tri-t-butyl-phosphine (0.78 mmol), 5.61 g of sodium t-butoxide (58.3 mmol), and 10.0 g of 4-bromophenyl pivalate (38.9 mmol) in 60 mL of dry toluene was stirred at room temperature under inert atmosphere for 18 h. The reaction mixture was filtered and the collected precipitate was washed with CH$_2$Cl$_2$ and discarded. The filtrate was concentrated in vacuo and the residue was chromatographed on silica gel with 5% ethyl acetate in hexanes to afford 8.6 g of pure N-(4'-pivaloyl-oxyphenyl)acridan.

$^1$H-NMR: (CDCl$_3$) ∂1.41 (s, 9H), 4.22 (s, 2H), 6.22 (d, 2H), 6.85 (t, 2H), 6.95 (t, 2H), 7.14 (d, 2H), 7.33 (s, 4H).

Example 19
Synthesis of N-(4'-nitrophenyl)acridan

A mixture of 10.00 g of acridan (55.2 mmol), 0.26 g of Pd(OAc)$_2$ (0.11 mmol), 0.20 g of tri-t-butylphosphine (0.88 mmol), 7.96 g of sodium t-butoxide (82.8 mmol), and 12.39 g of 1-bromo-4-nitrobenzene (61.3 mmol) in 150 mL of dry toluene (MgSO$_4$) was stirred at room temperature under inert atmosphere for 18 h. The reaction mixture was extracted with 1 L of CH$_2$Cl$_2$ and filtered through silica gel. The filtrate chromatographed on silica gel with 2.5–5% ethyl acetate in hexanes to afford white solid that was triturated in hexanes, filtered and dried to yield 4.00 g (24%) of pure N-(4-nitrophenyl)acridan.

$^1$H-NMR: (CDCl$_3$) ∂4.15 (s, 2H), 6.35–6.38 (d, 2H), 6.94–7.06 (m, 4H), 7.20–7.26 (d, 2H), 7.50–7.54 (d, 2H), 8.40–8.45 (d, 2H).

Example 20
Synthesis of N-(3'-pivaloyl-oxyphenyl)acridan

A mixture of 1.0 g of acridan (5.5 mmol), 795.4 mg of sodium t-butoxide (8.3 mmol), 64.1 mg of Pd(OAc)$_2$ (0.29 mmol), 1.56 g of 3-bromophenyl pivalate (6.07 mmol), and 47.2 mg of tri-t-butylphosphine (0.23 mmol) in 30 mL of dry toluene was allowed to stir at room temperature for 2 h under inert atmosphere. The reaction mixture was filtered through a plug of silica gel which was washed with 500 mL of CH$_2$Cl$_2$. The filtrate was concentrated in vacuo and chromatographed on silica gel in 2.5% ethyl acetate in hexanes to afford a solid, which triturated in hexanes, filtered and dried to afford 829.9 mg of N-(3'-pivaloyl-oxyphenyl)acridan (42%).

$^1$H-NMR: (CDCl$_3$) ∂1.35 (s, 9H), 4.22 (s, 2H), 6.25–6.27 (d, 2H), 6.84–6.88 (t, 2H), 6.95–6.99 (t, 2H), 7.07–7.08 (s, 1H), 7.13–7.15 (d, 2H), 7.20–7.26 (m, 2H), 7.59–7.65 (t, 1H).

Example 21
Synthesis of N-(3'-hydroxyphenyl)acridan

A solution of 621.9 mg of N-(3'-pivaloyloxyphenyl) acridan in 20 mL of methanol containing 2.61 g of 1 M NaOH (2.6 mmol) was refluxed until TLC analysis showed the starting material had been consumed. The solvent was concentrated and the residue was dissolved in water and acidified with 1 M hydrochloric acid. The resulting precipitate was collected via suction filtration, taken up with methy.ene chloride, dried over sodium sulfate and concentrated to a crude oil. The oil was chromatographed on silica gel in 5% ethyl acetate in hexanes. The purified product was treated with hexanes and the resultant solid was collected by filtration to afford 315.8 mg of N-(3'-hydroxyphenyl)acridan (67%).

$^1$H-NMR: (CDCl$_3$) ∂4.22 (s, 2H), 6.25–6.28 (d, 2H), 6.80–6.98 (m, 7H), 7.12–7.15 (d, 2H), 7.44–7.50 (t, 1H).

Example 22
Synthesis of N-(4'-fluorophenyl)acridan 9.0 g of acridan (49.6 mmol), 446 mg of Pd(OAc)$_2$ (2 mmol), 321 mg of tri-t-butylphosphine, 7.16 g of sodium t-butoxide (74 mmol), and 9.6 g of 1-bromo-4-fluorobenzene (54 mmol) in 90 mL of dry toluene was stirred under argon at room temperature for 2 h. TLC showed the absence of starting material. The reaction mixture was filtered through a Büchner funnel and the solid washed with CH$_2$Cl$_2$. The filtrate was then concentrated in vacuo and the residue was taken up in CH$_2$Cl$_2$ and refiltered. The filtrate was concentrated to dryness and chromatographed on silica gel in 5% ethyl acetate in hexanes, changing to CH$_2$Cl$_2$. Fractions containing product were combined and concentrated to dryness to afford N-(4'-fluorophenyl)acridan.

$^1$H-NMR: (CDCl$_3$) ∂4.22 (s, 2H), 6.16–6.19 (d, 2H), 6.84–6.88 (t, 2H), 6.93–6.98 (t, 2H), 7.13–7.16, (d, 2H), 7.29–7.31 (d, 4H).

Example 23
Synthesis of N-[4-(Benzothiazol-2-yl)-phenyl]acridan

A solution of 15.0 g of 4-bromobenzoic acid (74 mmol) and 13.9 g of 2-aminothiophenol (110 mmol) in 250 mL of dry toluene was heated to 45° C. and 10.1 mL of phosphorus trichloride (110 mmol) was slowly added to the reaction mixture via syringe. The mixture was allowed to reflux for 4 h. The reaction mixture was cooled to room temperature, filtered and the filtrate was concentrated under reduced pressure to afford a yellow solid. The solid was slowly added to 500 mL of saturated aq. NaHCO$_3$ and the aqueous solution was extracted with 2×200 mL of ethyl acetate. The combined organic solutions were washed with water (3x), dried over sodium sulfate and concentrated to dryness. The crude product was purified by column chromatography to afford 6.0 g of 2-(4-bromophenyl)benzothiazole.

$^1$H-NMR: (CDCl$_3$) ∂7.38–7.43 (t, 1H), 7.48–7.54 (t, 1H), 7.62–7.65 (d, 2H), 7.90–7.93 (d, 1H), 7.96–7.98 (d, 2H), 8.06–8.09 (d, 1H).

A mixture of 3.74 g of acridan (20 mmol), 69 mg of Pd(OAc)$_2$ (0.3 mmol), 44 mg of tri-t-butylphosphine (0.22 mmol), 2.88 g of sodium t-butoxide (30 mmol), and 6.0 g of 2-(4-bromophenyl)benzothiazole (20 mmol) in 60 mL of toluene was stirred at room temperature for 1 h under inert atmosphere, followed by heating at 50° C. for 1 h. The reaction mixture was cooled to room temperature, filtered and concentrated under reduced pressure. The crude product was purified by column chromatography with 15% ethyl acetate in hexanes. NMR analysis confirmed that 3.1 g of the N-arylated acridan product was isolated.

$^1$H-NMR: (CDCl$_3$) ∂4.25 (s, 2H), 6.27–6.30 (d, 2H), 6.86–6.91 (t, 2H), 6.95–7.00 (t, 2H), 7.16–7.18 (d, 2H), 7.41–7.57 (m, 4H), 7.95–7.97 (d, 1H), 8.11–8.14 (d, 1H), 8.33–8.36 (d, 2H).

Example 24
Synthesis of N-Anthracenylacridan

A mixture of 10.00 g of acridan (55.2 mmol), 247.7 mg of Pd(OAc)2 (1.10 mmol), 178.6 mg of tri-t-butylphosphine (0.88 mmol), 7.95 g of sodium t-butoxide (82.7 mmol), and 15.61 g of 9-bromoanthracene (60.7 mmol) in 100 mL of dry toluene was allowed to stir under inert atmosphere for 1 h. An additional 200 mL of toluene was added to the mixture and stirring was continued at room temperature for 30 min. The reaction mixture was poured into a mixture of 600 mL of $CH_2Cl_2$ and 100 g of silica gel. After stirring 15 min, the mixture was filtered, and the solid material was washed with an acditional 600 mL of $CH_2Cl_2$. The filtrate was concentrated in vacuo to afford a thick liquid, which was treated with 500 mL of hexanes. After stirring 15 min, the precipitate was collected by filtration, washed with 500 mL of hexanes, and dried. The solid was then triturated in 500 mL of hexanes for 1 h, filtered and dried to afford 14.39 g of N-anthracenylacridan by $^1$H-NMR analysis. The mother liquor was concentrated to a yellow solid which was trituratec in 300 mL of hexanes for 15 min. The precipitate was collected by filtration, washed with 200 mL of hexanes and dried to afford 5.40 g of solid. $^1$H-NMR analysis showed the second crop of product was slightly less pure than the first. The two lots were combined to afford 19.79 g of the N-anthracenylacridan (100%).

$^1$H-NMR: ($CDCl_3$) ∂4.52 (s, 2H), 5.70–5.73 (d, 2H), 6.69–6.74 (t, 2H), 6.80–6.85 (t, 2H), 7.22–7.25 (d, 2H), 7.35–7.40 (t, 2H), 7.47–7.51 (t, 2H), 7.91–7.94 (d, 2H), 8.12–8.15 (d, 2H), 8.63 (s, 1H).

Example 25
Synthesis of N-Pyrenylacridan

A mixture of 10.00 g of acridan (55.2 mmol), 247.7 mg of $Pd(OAc)_2$ (1.10 mmol), 178.6 mg of tri-t-butylphosphine (0.88 mmol), 7.95 g of sodium t-butoxide (82.7 mmol), and 17.06 g of 1-bromopyrene (60.7 mmol) in 100 mL of dry toluene was allowed to stir under inert atmosphere. The exothermic reaction heated to reflux, causing a precipitate to form. An additional 200 mL of toluene was added to the mixture and stirring was continued at room temperature for 1 h. The reaction mixture was poured into a mixture of 600 mL of $CH_2Cl_2$ and 100 g of silica gel. The mixture was filtered, and the solid material was washed with 600 mL of $CH_2Cl_2$. The filtrate was concentrated in vacuo to afford a thick liquid containing a precipitate. The precipitate was collected by filtration, washed with 300 mL of toluene and 500 mL of hexanes, and dried to afford 12.69 g of N-pyrenylacridan by $^1$H-NMR analysis. The mother liquor was concentrated to a yellow solid which was triturated in 300 mL of hexanes for 30 min. The precipitate was collected by filtration, washed with 200 mL of hexanes and dried to afford 7.46 g of solid. $^1$H-NMR analysis showed the second crop of product was slightly less pure than the first. The two lots were combined to afford 20.15 g of the N-pyrenylacridan (95.7%).

$^1$H-NMR: ($CDCl_3$) ∂4.45 (s, 2H), 5.93–5.96 (d, 2H), 6.76–6.87 (m, 4H), 7.22–7.25 (d, 2H), 7.98–8.06 (m, 4H), 8.17–8.27 (m, 4H), 8.37–8.40 (d, 1H).

Example 26
Synthesis of N-(4'-Cyanophenyl)acridan

A solution of 10.00 g of acridan (55.2 mmol), 10.48 g of 4-bromobenzonitrile (57.6 mmol), 7.89 g of sodium t-butoxide (82.1 mmol), 0.18 g of $Pd(OAc)_2$ (0.80 mmol), and 0.1245 g of tri-t-butylphosphine (0.62 mmol) in 100 mL of dry toluene was stirred for 18 h at room temperature and 7 h at reflux under inert atmosphere. 0.12 g of $Pd(OAc)_2$ (0.53 mmol) and 0.09 g of tri-t-butylphosphine (0.44 mmol) were added to the reaction mixture which was refluxed for an additional 4 h. The reaction mixture was concentrated to a thick slurry and was chromatographed on silica gel with 5% ethyl acetate in hexanes to afford 11.67 g of impure product. A solution of the combined solids in 100 mL of $CH_2Cl_2$ was treated with 5 mL of oxalyl chloride and allowed to stir for 1 h. The reaction mixture was extracted with aqueous $NaHCO_3$, and the organic layer was concentrated to an orange solid. The solid was purified by chromatography on silica with 2% ethyl acetate in hexanes to afford 4.81 g of N-(4'-cyanophenyl)acridan (30.9%).

$^1$H-NMR: ($CDCl_3$) ∂4.19 (s, 2H), 6.19–6.22 (d, 2H), 6.90–7.01 (m, 4H), 7.18–7.26 (d, 2H), 7.46–7.49 (d, 2H), 7.89–7.92 (d, 2H).

Example 27
Synthesis of N-(4'-(4"-Pivaloyl)biphenyl)-acridan

A solution of 20.00 g of N-(4'-(4"-Hydroxybiphenyl))-acridan (80.3 mmol) in 200 mL of dry THF under inert atmosphere was treated with 10.4 mL of pivaloyl chloride (84.3 mmol), followed by 24.0 mL of dry triethylamine (KOH) (169 mmol). The solution was stirred 30 min at room temperature, forming a precipitate. 1.0 mL of pivaloyl chloride was added to the reaction, and after 15 min, the precipitate was collected by vacuum filtration, washed with 100 mL of THF and discarded. The filtrate was concentrated in vacuo and dried to afford 27.33 g of a white solid. $^1$H-NMR analysis confirms that 4-(4'-bromophenyl)phenyl pivalate was isolated (102%).

$^1$H-NMR: ($CDCl_3$) ∂1.38 (s, 9H), 7.11–7.14 (d, 2H), 7.41–7.44 (d, 2H), 7.53–7.57 (m, 4H).

A mixture of 10.00 g of acridan (55.2 mmol), 247.7 mg of Pd(OAc)2 (1.10 mmol), 178.6 mg of tri-t-butylphosphine (0.88 mmol), 7.95 g of sodium t-butoxide (82.7 mmol), and 20.22 g of 4-(4'-bromophenyl)phenyl pivalate (60.7 mmol) in 60 mL of dry toluene was placed under inert atmosphere. The exothermic reaction mixture stirred at room temperature for 1 h, when TLC analysis showed the starting material was consumed. 600 mL of $CH_2Cl_2$ and 100 g of silica gel was added to the reaction mixture. After stirring 15 min, the mixture was filtered, and the solid material was washed with an additional 600 mL of $CH_2Cl_2$. The filtrate was concentrated in vacuo to afford a thick liquid, which was treated with 500 mL of hexanes. After stirring 18 h, the precipitate was collected by filtration, washed with 300 mL of hexanes, and dried to afford 21.63 g of N-(4'-(4"-pivaloyl)biphenyl)acridan (90%).

$^1$H-NMR: ($CDCl_3$) ∂1.40 (s, 9H), 4.24 (s, 2H), 6.27–6.30 (d, 2H), 6.84–6.89 (t, 2H), 6.94–6.99 (t, 2H), 7.14–7.21 (m, 4H), 7.37–7.40 (d, 2H), 7.67–7.70 (d, 2H), 7.79–7.81 (d, 2H).

Example 28
Synthesis of N-Pyridylacridan

A mixture of 10.00 g of acridan (55.2 mmol), 247.7 mg of Pd(OAc)2 (1.10 mmol), 178.6 mg of tri-t-butylphosphine (0.88 mmol), 7.95 g of sodium t-butoxide (82.7 mmol), and 6.3 mL of 2-bromopyridine (66.2 mmol) in 100 mL of dry toluene was allowed to stir under inert atmosphere for 18 h. The reaction mixture was poured into a mixture of 300 mL of $CH_2Cl_2$ and 100 g of silica gel with stirring. The mixture was filtered, and the solid material was washed with 1 L of $CH_2Cl_2$. The filtrate was concentrated in vacuo to afford a yellow oil, which was taken up in hexanes. The semi-solution was again concentrated in vacuo to afford a yellow solid. The solid was triturated in 100 mL of hexanes for several hours, filtered and dried to afford 12.50 g of N-pyridylacridan (88%).

$^1$H-NMR: (CDCl3) ∂4.12 (s, 2H), 6.59–6.62 (d, 2H), 6.91–6.96 (t, 2H), 7.00–7.05 (t, 2H), 7.17–7.20 (d, 2H), 7.28–7.35 (m, 2H), 7.81–7.87 (m, 1H), 8.69–8.70 (d, 1H).

Chemiluminescence Measurements

The experiments in the following examples were performed using either a Turner Designs TD-20e (Sunnyvale, Calif.) luminometer fitted with neutral density filter for light attenuation or a Labsystems Luminoskan (Helsinki, Finland) luminometer. Data collection, analysis and display were software controlled.

Example 29
Chemiluminescent Formulations for Peroxidase Detection

A preferred formulation for producing chemiluminescence using an N-arylacridancarboxylic acid derivative of the present invention in a reaction with a peroxidase enzyme contains the following components:

(1) 0.01 M tris buffer, pH 8.0
(2) 0.05 mM acridan compound 1
(3) 0.5 mM urea peroxide
(4) 0.1 mM p-phenylphenol
(5) 0.025% TWEEN 20
(6) 1 mM EDTA.

The reagent in final form also contained p-Dioxane 1.25% and Ethanol 1.25% used for solubilization purposes.

Example 30
Comparison of the Light Intensity-Time Profile for Detection of HRP with Compounds 1b-1,p,q. In separate experiments, 100 µL volumes of solutions of each of compound 1b-l, 1p and 1q were reacted with 1 µL of a solution containing $1.4 \times 10^{-16}$ mol of HRP in water. The formulations were prepared according to Example 29. Table 4 gives the maximum light intensity values obtained under these conditions.

TABLE 4

Relative Intensities and other tests on N-arylacridans.

| Compound | $I_{max}$ | @ Time (min) |
|---|---|---|
| 1b | 344 | 60 |
| 1c | 1014 | 60 |
| 1d | 78 | 60 |
| 1e | 110 | 30 |
| 1f | 61 | 60 |
| 1g | 35 | 60 |
| 1h | 32 | 60 |
| 1i | 15 | 30 |
| 1j | 11.5 | 60 |
| 1k | 100 | 60 |
| 1l | 2.3 | 60 |
| 1p | 335 | 30 |
| 1q | 135 | 40 |

Example 31
Improved Chemiluminescent Detection of Proteins by Western Blot

Chemiluminescent western blots were performed to demonstrate the utility of N-arylacridan-carboxyl acid derivatives in methods for detecting peroxidase conjugates of a biomolecule. Detection reagents containing each of Compounds 1b–1e were used. β-Galactosidase, mouse anti-β-galactosidase IgG and sheep anti-mouse IgG peroxidase conjugated Fab fragments were obtained from Roche Molecular Products (Indianapolis, Ind.). The IgG sample was centrifuged at 10,000×g for 2 min and the supernatant was used in the immunological reaction.

SDS-PAGE was performed utilizing the buffer system described by LaemmLi (U. K. Laemmli, Nature (London), 227, 680 (1970)). The stacking gel was 4.38% acrylamide: 0.12% bisacrylamide. The separating gel was 6.81% acrylamide: 0.19% bisacrylamide. Following electrophoresis the gel was equilibrated for 7–8 min with the transfer buffer which contained 20 mM Tris, 153 mM glycine and 20% (v/v) methanol. The gel, sandwiched between a sheet of PVDF transfer membrane and a sheet of chromatography paper 3MM (Whatman), was placed in the transfer unit (Bio-Rad Laboratories, Richmond, Calif.). The proteins in the gel were electroeluted for 25 min at 4° C. at a 100 V constant voltage. The membrane was then placed in 50 mM Tris-HCl buffered saline at pH 7.4 (TBS) at 4° C. overnight. After this period the membrane was washed with TBS for 15 min.

The membrane was treated with 0.05% TWEEN-20 in 50 mM Tris-HCl buffered saline at pH 7.4 (T-TBS) containing 1% non-fat powdered milk (NFM) for 1 hr at room temperature. This blocked membrane was incubated for 75 min at room temperature with primary antibody (1:1500 dilution of 3.3 µg,/mL mouse anti-β-galactosidase IgG fraction) using T-TBS containing 1% NFM.

The membrane was then rinsed and washed twice for 10 min each with T-TBS at room temperature and then twice for 10 min each with 1% NFM in T-TBS. The washed membrane was incubated for 30 min at room temperature with secondary antibody (67 mU/mL, 1:600 dilution of anti-mouse IgG peroxidase conjugated Fab fragments) using T-TBS containing 1% NFM. The membrane was rinsed and washed four times for 15 min each with T-TBS.

The washed membrane was soaked in a detection reagent for 3 min, drained and placed between sheets of transparency film. The X-ray film was exposed to the membrane for varying periods of time and developed. The composition of detection reagent solution containing the acridan compounds was:

| Tris buffer, pH 8.0 | 0.025M |
|---|---|
| Acridan 1b, c, d or e | 0.05 mM |
| p-Iodophenol | 2 mM |
| TWEEN 20 | 0.1% (w/w) |
| Urea peroxide | 2.5 mM |
| EDTA | 0.5 mM |
| p-Dioxane | 1.25% |
| Ethanol | 1.25% |

The β-galactosidase standards utilized (5 ng to 5 pg) were clearly visible down to 5 pg/slot over the background. It was possible to make several exposures of the membrane during a period of 24 h as the membrane continued to emit light.

It is intended that the foregoing description be only illustrative of the present invention and that the present invention be limited only by the appended claims.

We claim:

1. A process for preparing an N-arylacridancarboxylic acid derivative of the formula (1):

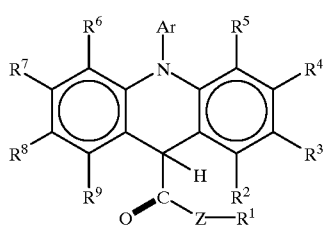

wherein $R^1$ is selected from alkyl, substituted alkyl, heteroalkl, aralkyl, substituted aralkyl, aryl, substituted aryl and heteroaryl groups, Z is selected from O and S atoms or the group $ZR^1$ is an —$NR^{10}R^{11}$ group wherein $R^{10}$ and $R^{11}$ are independently selected from alkyl, substituted alkyl, aryl, substituted aryl, aralkyl, alkylsulfonyl and arylsulfonyl groups, and wherein $R^{10}$ and $R^{11}$ can be combined with N into a heterocycle with leaving group ability, each of $R^2$–$R^9$ is independently selected from substituents which contain from 1 to 50 atoms selected from C, H, N, O, S, P and halogen atoms and wherein Ar is selected from aryl, substituted aryl and heteroaryl groups, the process comprising the steps of:

a) reducing an acridone compound (2) having the formula:

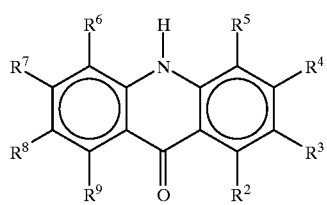

(2)

wherein $R^2$–$R^9$ are as defined above to an acridan compound (3) having the formula:

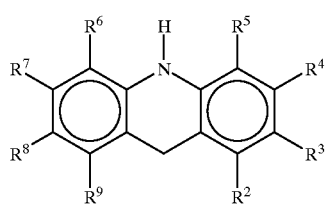

(3)

wherein $R^2$–$R^9$ are as defined above;

b) converting the acridan compound (3) to an N-arylacridan compound (4) having the formula:

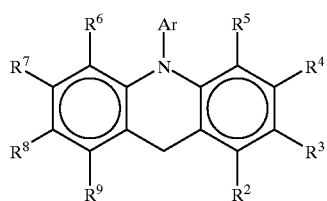

(4)

wherein $R^2$–$R^9$ are as defined above and Ar is an aryl, substituted aryl or heteroaryl ring group by reacting the acridan compound with an arylating compound selected from aryl, substituted aryl and heteroaryl halides and aryl, substituted aryl and heteroaryl sulfonate esters in an inert solvent in the presence of a base and a palladium catalyst; and c) converting the N-arylacridan (4) to the N-arylacridancarboxylic acid derivative by a carboxylation reaction in which a carbonyl-containing group is attached to the 9-position of the acridan ring.

2. The process of claim 1 wherein the palladium catalyst is prepared from a divalent palladium compound $PdL_2$ and a tertiary phosphine $PR_3$, wherein each L is a labile ligand and where n each R is independently selected from alkyl and aryl groups.

3. The process of claim 2 wherein the tertiary phosphine is selected from $P(t-Bu)_3$, BINAP, DPPE, DPPF, DPPB and DPPP.

4. The process of claim 2 wherein the ligand L is selected from carboxylate esters, halogens and ketones.

5. The process of claim 1 wherein acridone compound (2) is reduced by reaction with a reducing agent selected from Na/Hg amalgam, Al/Hg amalgam, copper chromite, $NH_2NH_2$ and a hydride reducing agent.

6. The process of claim 1 wherein the group Ar is selected from pheryl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl and pyrrolyl groups any of which can contain one or more substituents selected from halogen, trihalomethyl, nitro, nitroso, cyano, ammonium, hydrazinyl, carboxyl, carboxamide, carboalkoxy, —CHO, keto, amino, substituted amino, imino, amido, aryl, alkyl, perfluoroalkyl, alkenyl, alkynyl, alkoxy, hydroxy, sulfhydryl, alkylthio, sulfate, sulfonate, phosphonium, phosphate and phosphonate groups.

7. The process of claim 1 wherein the group —$NR^{10}R^{11}$ is a cyclic group selected from pyrazole, imidazole, benzimidazole, triazole, benzotriazole, tetrazole, oxazole, benzoxazole, thiazole and benzothiazole.

8. The process of claim 1 wherein in the group —$NR^{10}R^{11}$ one of $R^{10}$ and $R^{11}$ is alkylsulfonyl or arylsulfonyl and the other of $R^{10}$ or $R^{11}$ is an alkyl, phenyl or substituted phenyl group.

9. The process of claim 1 wherein Z is O or S and $R^1$ is selected from substituted alkyl and substituted aryl groups which are substituted with at least one electron withdrawing group.

10. The process of claim 9 wherein the electron withdrawing group is a halogen atom.

11. The process of claim 9 wherein $R^1$ is a trifluorophenyl group.

12. The process of claim 1 wherein each of $R^2$ to $R^9$ is hydrogen.

13. The process of claim 1 wherein step c comprises:
(i) reacting the N-arylacridan (4) with a base to generate an anion of the N-arylacridan;
(ii) capturing the anion with $CO_2$ to produce an N-arylacridancarboxylic acid (5) having the formula:

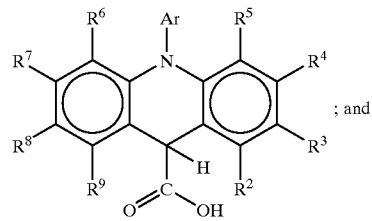

(5)

; and (iii) reacting the N-arylacridancarboxylic acid with a compound $HZ-R^1$ to form compound (1).

14. The process of claim 13 wherein a coupling agent is used in the reaction to convert the N-arylacridancarboxylic acid to the acid derivative and the coupling agent is selected from thionyl chloride, $PCl_3$, a carbodiimide, carbonyl diimidazole, strong acids and bases.

15. The process of claim 1 wherein step c comprises:
(i) reacting the N-arylacridan (4) with a base to generate an anion of the N-arylacridan;
(ii) reacting the anion with a reagent having the formula X—CO—$ZR^1$ wherein X is a leaving group.

16. A process for preparing an N-arylacridancarboxylic acid derivative of the formula (1):

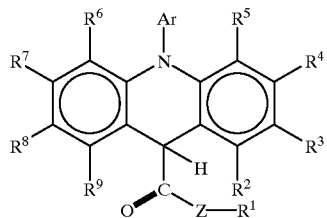

(1)

wherein $R^1$ is selected from alkyl, substituted alkyl, heteroalkyl, aralkyl, substituted aralkyl, aryl, substituted aryl and heteroaryl groups, Z is selected from O and S atoms or the group $ZR^1$ is an —$NR^{10}R^{11}$ group wherein $R^{10}$ and $R^{11}$ are independently selected from alkyl, substituted alkyl, aryl, substituted aryl, aralkyl, alkylsulfonyl and arylsulfonyl groups, and wherein $R^{10}$ and $R^{11}$ can be combined with N into a heterocycle with leaving group ability, each of $R^2$–$R^9$ is independently selected from substituents which contain from 1 to 50 atoms selected from C, H, N, O, S, P and halogen atoms and wherein Ar is selected from aryl, substituted aryl and heteroaryl groups, the process comprising converting an acridancarboxylic acid derivative (6)

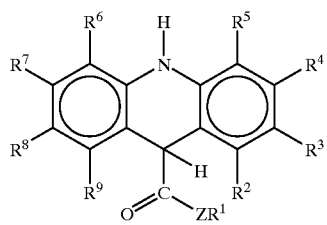

(6)

having groups Z and $R^1$–$R^9$ as defined above to the N-arylacridancarboxylic acid derivative (1) by reacting the compound (6) with an arylating compound selected from aryl, substituted aryl and heteroaryl halides and aryl, substituted aryl and heteroaryl sulfonate esters in an inert solvent in the presence of a base and a palladium catalyst.

17. The process of claim 16 wherein the palladium catalyst is prepared from a divalent palladium compound $PdL_2$ and a tertiary phosphine $PR_3$, wherein each L is a labile ligand and wherein each R is independently selected from alkyl and aryl groups.

18. The process of claim 17 wherein the tertiary phosphine is selected from $P(t-Bu)_3$, BINAP, DPPE, DPPF, DPPB and DPPP.

19. The process of claim 17 wherein the ligand L is selected from carboxylate esters, halogens and ketones.

20. The process of claim 16 wherein the group Ar is selected from phenyl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl and pyrrolyl groups any of which can contain one or more substituents selected from halogen, trihalomethyl, nitro, nitroso, cyano, ammonium, hydrazinyl, carboxyl, carboxamide, carboalkoxy, —CHO, keto, amino, substituted amino, irrino, amido, aryl, alkyl, perfluoroalkyl, alkenyl, alkynyl, alkoxy, hydroxy, sulfhydryl, alkylthio, sulfate, sulfonate, phosphonium, phosphate and phosphonate groups.

21. A process for preparing an N-arylacridancarboxylic acid derivative of the formula (1):

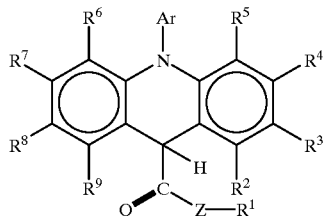

(1)

wherein $R^1$ is selected from alkyl, substituted alkyl, heteroalkyl, aralkyl, substituted aralkyl, aryl, substituted aryl and heteroaryl groups, Z is selected from O and S atoms or the group $ZR^1$ is an —$NR^{10}R^{11}$ group wherein $R^{10}$ and $R^{11}$ are independently selected from alkyl, substituted alkyl, aryl, substituted aryl, aralkyl, alkylsulfonyl and arylsulfonyl groups, and wherein $R^{10}$ and $R^{11}$ can be combined with N into a heterocycle with leaving group ability, each of $R^2$–$R^9$ is independently selected from substituents which contain from 1 to 50 atoms selected from C, H, N, O, S, P and halogen atoms and wherein Ar is selected from aryl, substituted aryl and heteroaryl groups, the process comprising the steps of:

a) converting an acridancarboxylic acid (7)

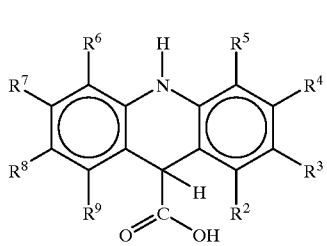

(7)

to an N-arylacridancarboxylic acid (5) by reacting the acridancarboxylic acid (7) with an arylating compound selected from aryl, substituted aryl and heteroaryl halides and aryl, substituted aryl and heteroaryl sulfonate esters in an inert solvent in the presence of a base and a palladium catalyst; and b) reacting the N-arylacridancarboxylic acid (5) with a compound HZ—$R^1$ wherein Z and $R^1$ are as defined above to form compound (1).

22. The process of claim 21 wherein a coupling agent is used in the reaction to convert the N-arylacridancarboxylic acid to the acid derivative and the coupling agent is selected from thionyl chloride, $PCl_3$, a carbodiimide, carbonyl diimidazole, strong acids and bases.

23. The process of claim 21 wherein the palladium catalyst is prepared from a divalent palladium compound $PdL_2$ and a tertiary phosphine $PR_3$, wherein each L is a labile ligand and wherein each R is independently selected from alkyl and aryl groups.

24. The process of claim 23 wherein the tertiary phosphine is selected from $P(t-Bu)_3$, BINAP, DPPE, DPPF, DPPB and DPPP.

25. The process of claim 23 wherein the ligand L is selected from carboxylate esters, halogens and ketones.

26. The process of claim 21 wherein the group Ar is selected from phenyl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl and pyrrolyl groups any of which can contain one or more substituents selected from halogen, trihalomethyl, nitro, nitroso, cyano, ammonium, hydrazinyl, carboxyl, carboxamide, carboalkoxy, —CHO, keto, amino, substituted amino, imino, amido, aryl, alkyl, perfluoroalkyl, alkenyl, alkynyl, alkoxy, hydroxy, sulfhydryl, alkylthio, sulfate, sulfonate, phosphonium, phosphate and phosphonate groups.

27. A process for preparing an N-arylacridancarboxylic acid derivative of the formula (1):

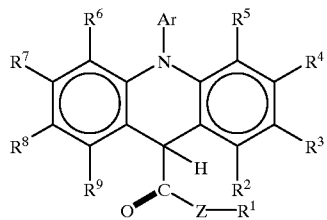

(1)

wherein $R^1$ is selected from alkyl, substituted alkyl, heteroalkyl, aralkyl, substituted aralkyl, aryl, substituted aryl and heteroaryl groups, Z is selected from O and S atoms or the group $ZR^1$ is an —$NR^{10}R^{11}$ group wherein $R^{10}$ and $R^{11}$ are independently selected from alkyl, substituted alkyl, aryl, substituted aryl, aralkyl, alkylsulfonyl and arylsulfonyl groups, and wherein $R^{10}$ and $R^{11}$ can be combined with N into a heterocycle with leaving group ability, each of $R^2$–$R^9$ is independently selected from substituents which contain from 1 to 50 atoms selected from C, H, N, O, S, P and halogen atoms and wherein Ar is selected from aryl, substituted aryl and heteroaryl groups, comprising the steps of:

a) converting an acridone compound (2) having the formula:

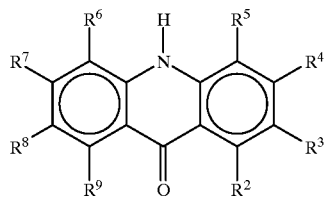

(2)

wherein $R^2$–$R^9$ are as defined above to an N-arylacridone compound (8) having the formula:

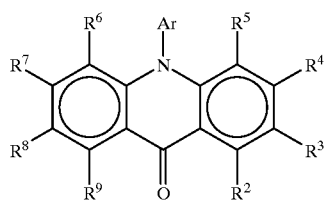

(8)

wherein Ar and $R^2$–$R^9$ are as defined above with an arylating compound selected from aryl, substituted aryl and heteroaryl halides and aryl, substituted aryl and heteroaryl sulfonate esters in an inert solvent in the presence of a base and a palladium catalyst wherein $R^2$–$R^9$ are as defined above;

b) reducing the N-arylacridone compound (8) to an N-arylacridan compound (4) having the formula:

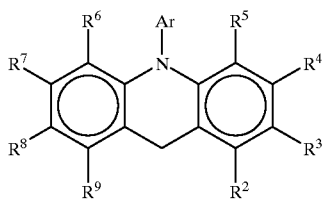

(4)

wherein Ar and $R^2$–$R^9$ are as defined above; and c) converting the N-arylacridan (4) to the N-arylacridancarboxylic acid derivative by a carboxylation reaction in which a carbonyl-containing group is attached to the 9-position of the acridan ring.

28. The process of claim 27 wherein the palladium catalyst is prepared from a divalent palladium compound $PdL_2$ and a tertiary phosphine $PR_3$, wherein each L is a labile ligand and wherein each R is independently selected from alkyl and aryl groups.

29. The process of claim 28 wherein the tertiary phosphine is selected from $P(t-Bu)_3$, BINAP, DPPE, DPPF, DPPB and DPPP.

30. The process of claim 28 wherein the ligand L is selected from carboxylate esters, halogens and ketones.

31. The process of claim 27 wherein the group Ar is selected from phenyl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl and pyrrolyl groups any of which can contain one or more substituents selected from halogen, trihalomethyl, nitro, nitroso, cyano, ammonium, hydrazinyl, carboxyl, carboxamide, carboalkoxy, —CHO, keto, amino, substituted amino, imino, amido, aryl, alkyl, perfluoroalkyl, alkenyl, alkynyl, alkoxy, hydroxy, sulfhydryl, alkylthio, sulfate, sulfonate, phosphonium, phosphate and phosphonate groups.

32. A compound having the formula:

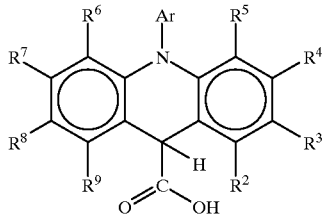

or a salt thereof wherein each of $R^2$–$R^9$ is independently selected from substituents which contain from 1 to 50 atoms selected from C, H, N, O, S, P and halogen atoms and wherein Ar is selected from aryl, substituted aryl and heteroaryl groups.

33. The compound of claim 32 wherein the group Ar is selected from phenyl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl and pyrrolyl groups any of which can contain one or more substituents selected from halogen, trihalomethyl, nitro, nitroso, cyano, ammonium, hydrazinyl, carboxyl, carboxamide, carboalkoxy, —CHO, keto, amino, substituted amino, imino, amido, aryl, alkyl, perfluoroalkyl, alkenyl, alkynyl, alkoxy, hydroxy, sulfhydryl, alkylthio, sulfate, sulfonate, phosphonium, phosphate and phosphonate groups.

34. The compound of claim 33 wherein Ar is selected from phenyl, substituted phenyl, naphthyl and substituted naphthyl.

35. The compound of claim 32 wherein each of $R^2$–$R^9$ is a hydrogen.

36. The compound of claim 34 wherein each of $R^2$–$R^9$ is a hydrogen.

37. The compound of claim 32 wherein the salt is selected from alkali metal salts.

38. A compound of the formula (1):

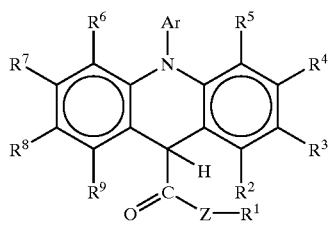

(1)

wherein $R^1$ is selected from alkyl, substituted alkyl, heteroalkyl, aralkyl, substituted aralkyl, aryl, substituted aryl and heteroaryl groups, Z is selected from O and S atoms or the group $ZR^1$ is an —$NR^{10}R^{11}$ group wherein $R^{10}$ and $R^{11}$ are independently selected from alkyl, substituted alkyl, aryl, substituted aryl, aralkyl, alkylsulfonyl and arylsulfonyl groups, and wherein $R^{10}$ and $R^{11}$ can be combined with N into a heterocycle with leaving group ability, each of $R^2$—$R^9$ is independently selected from substituents which contain from 1 to 50 atoms selected from C, H, N, O, S, P and halogen atoms and wherein Ar is selected from aryl, substituted aryl and heteroaryl groups, prepared by a process comprising the steps of:

a) reducing an acridone compound (2) having the formula:

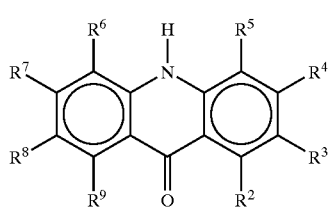

(2)

wherein $R^2$—$R^9$ are as defined above to an acridan compound (3) having the formula:

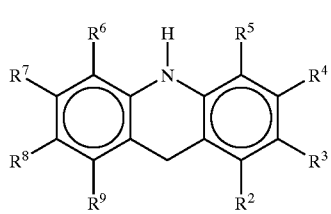

(3)

wherein $R^2$—$R^9$ are as defined above;

b) converting the acridan compound (3) to an N-arylacridan compound (4) having the formula:

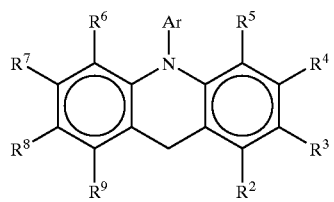

(4)

wherein $R^2$—$R^9$ are as defined above and Ar is an aryl, substituted aryl or heteroaryl ring group by reacting the acridan compound with an arylating compound selected from aryl, substituted aryl and heteroaryl halides and aryl, substituted aryl and heteroaryl sulfonate esters in an inert solvent in the presence of a base and a palladium catalyst; and c) converting the N-arylacridan (4) to the N-arylacridancarboxylic acid derivative by a carboxylation reaction in which a carbonyl-containing group is attached to the 9-position of the acridan ring.

39. The compound of claim 38 wherein the group Ar is selected from phenyl, naphthyl, biphenyl, anthryl, pyrenyl, pyridyl, quinolyl, acridinyl, furyl, xanthenyl, thienyl, thioxanthyl, thiazolyl, benzothiazolyl, indolyl, imidazolyl, and pyrrolyl groups any of which can contain one or more substituents selected from halogen, trihalomethyl, nitro, nitroso, cyano, ammonium, hydrazinyl, carboxyl, carboxamide, carboalkoxy, —CHO, keto, amino, substituted amino, imino, imido, aryl, alkyl, perfluoroalkyl, alkenyl, alkynyl, alkoxy, hydroxy, sulfhydryl, alkylthio, sulfate, sulfonate, phosphonium, phosphate and phosphonate groups.

40. The compound of claim 38 wherein the group —$NR^{10}R^{11}$ is a cyclic group selected from pyrazole, imidazole, benzimidazole, triazole, benzotraizole, tetrazole, oxazole, benzoxazole, thiazole, and benzothiazole.

41. The compound of claim 38 wherein the group —$NR^{10}R^{11}$ one of $R^{10}$ and $R^{11}$ is alkylsulfonyl or arylsulfonyl and the other of $R^{10}$ and $R^{11}$ is an alkyl, phenyl or substituted phenyl group.

42. The compound of claim 38 wherein Z is O or S and $R^1$ is selected from substituted alkyl an substituted aryl groups which are substituted with at least one electron withdrawing group.

43. The compound of claim 42 wherein the electron withdrawing group is a halogen atom.

44. The compound of claim 42 wherein $R^1$ is a trifluorophenyl group.

45. The compound of claim 38 wherein each of $R^2$ to $R^9$ is hydrogen.

46. The compound of claim 38 wherein the carboxylation reaction step (c) comprises:

(i) reacting the N-arylacridan (4) with a base to generate an anion of the N-arylacridan;

(ii) capturing the anion with $CO_2$ to produce an N-arylacridancarboxylic acid (5) having the formula:

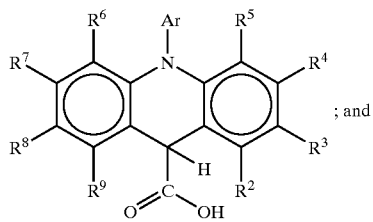

(5)

(iii) reacting the N-arylacridancarboxylic acid with a compound HZ—R¹ to form compound (1).

47. The compound of claim 38 wherein the palladium catalyst of step (b) of the process is prepared from a divalent palladium compound $PdL_2$ and a tertiary phosphine $PR_3$, wherein each L is a labile ligand and wherein each R is independently selected from alkyl and aryl groups.

48. The compound of claim 38 wherein the tertiary phosphine of step (b) of the process is selected from P(t—Bu)₃, BINAP, DPPE, DPPF, DPPB and DPPP.

49. The compound of claim 47 wherein the ligand L is selected from carboxylate esters, halogens and ketones.

50. The compound of claim 38 wherein acridone compound (2) is reduced in step (a) of the process by reaction with a reducing agent selected from Na/Hg amalgam, Al/Hg amalgam, copper chromite, $NH_2NH_2$ and a hydride reducing agent.

\* \* \* \* \*